(12) United States Patent
Al-Ali et al.

(10) Patent No.: US 10,918,341 B2
(45) Date of Patent: Feb. 16, 2021

(54) PHYSIOLOGICAL PARAMETER SYSTEM

(71) Applicant: MASIMO CORPORATION, Irvine, CA (US)

(72) Inventors: Ammar Al-Ali, San Juan Capistrano, CA (US); John Graybeal, Grantville, PA (US); Massi Joe E. Kiani, Laguna Niguel, CA (US); Michael Petterson, Dana Point, CA (US); Chris Kilpatrick, Irvine, CA (US)

(73) Assignee: Masimo Corporation, Irvine, CA (US)

( * ) Notice: Subject to any disclaimer, the term of this patent is extended or adjusted under 35 U.S.C. 154(b) by 260 days.

(21) Appl. No.: 15/862,283

(22) Filed: Jan. 4, 2018

(65) Prior Publication Data

US 2018/0125430 A1 May 10, 2018

Related U.S. Application Data

(63) Continuation of application No. 14/507,415, filed on Oct. 6, 2014, now abandoned, which is a continuation (Continued)

(51) Int. Cl.
*A61B 5/00* (2006.01)
*A61B 5/0205* (2006.01)
(Continued)

(52) U.S. Cl.
CPC .......... *A61B 5/7282* (2013.01); *A61B 5/0004* (2013.01); *A61B 5/01* (2013.01); *A61B 5/021* (2013.01); *A61B 5/024* (2013.01); *A61B 5/0205* (2013.01); *A61B 5/0402* (2013.01); *A61B 5/08* (2013.01); *A61B 5/0816* (2013.01);
(Continued)

(58) Field of Classification Search
CPC ...... G16H 50/30; G16H 40/63; A61B 5/7282; A61B 5/0004; A61B 5/1455; A61B 5/4839; A61B 5/6832; A61B 5/6843; A61B 5/7246; A61B 5/7405; A61B 5/742; A61B 5/746; A61B 5/01; A61B 5/021; A61B 5/024; A61B 5/0402; A61B 5/0816; A61B 5/14532; A61B 5/14539; A61B 5/14546; A61B 5/08; A61B 5/14551; A61B 5/412; A61B 5/6826; A61B 5/6838; A61B 5/7221; A61B 5/0205; A61B 5/7275;
(Continued)

(56) References Cited

U.S. PATENT DOCUMENTS 4,960,128 A 10/1990 Gordon et al.
4,964,408 A 10/1990 Hink et al.
(Continued)

OTHER PUBLICATIONS

US 8,845,543 B2, 09/2014, Diab et al. (withdrawn)

*Primary Examiner* — Mark Bockelman
(74) *Attorney, Agent, or Firm* — Knobbe Martens Olson & Bear, LLP

(57) ABSTRACT

A physiological parameter system has one or more parameter inputs responsive to one or more physiological sensors. The physiological parameter system may also have quality indicators relating to confidence in the parameter inputs. A processor is adapted to combine the parameter inputs, quality indicators and predetermined limits for the parameters inputs and quality indicators so as to generate alarm outputs or control outputs or both.

10 Claims, 21 Drawing Sheets

Related U.S. Application Data of application No. 11/963,640, filed on Dec. 21, 2007, now Pat. No. 8,852,094.

(60) Provisional application No. 60/876,749, filed on Dec. 22, 2006.

(51) Int. Cl.

| | | |
|---|---|---|
| *A61B 5/021* | (2006.01) | |
| *A61B 5/01* | (2006.01) | |
| *A61B 5/1455* | (2006.01) | |
| *A61B 5/145* | (2006.01) | |
| *A61B 5/08* | (2006.01) | |
| *A61B 5/0402* | (2006.01) | |
| *A61B 5/024* | (2006.01) | |
| *G16H 50/30* | (2018.01) | |
| *G16H 40/63* | (2018.01) | |

(52) U.S. Cl.
CPC ........ *A61B 5/1455* (2013.01); *A61B 5/14532* (2013.01); *A61B 5/14539* (2013.01); *A61B 5/14546* (2013.01); *A61B 5/14551* (2013.01); *A61B 5/412* (2013.01); *A61B 5/4839* (2013.01); *A61B 5/6826* (2013.01); *A61B 5/6832* (2013.01); *A61B 5/6838* (2013.01); *A61B 5/6843* (2013.01); *A61B 5/7221* (2013.01); *A61B 5/7246* (2013.01); *A61B 5/7275* (2013.01); *A61B 5/742* (2013.01); *A61B 5/7405* (2013.01); *A61B 5/746* (2013.01); *G16H 40/63* (2018.01); *G16H 50/30* (2018.01); *A61B 5/082* (2013.01); *A61B 5/14552* (2013.01); *A61B 2560/0285* (2013.01); *A61B 2560/0443* (2013.01); *A61B 2562/222* (2013.01)

(58) Field of Classification Search
CPC .... A61B 2560/0285; A61B 2560/0443; A61B 2562/222; A61B 5/082; A61B 5/14552
See application file for complete search history.

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |

(56) References Cited

U.S. PATENT DOCUMENTS

| | | | |
|---|---|---|---|
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |

(56) References Cited

U.S. PATENT DOCUMENTS

| | | |
|---|---|---|
| 7,874,993 B2 * | 1/2011 | Bardy .................. A61B 5/0002 600/508 |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,909,772 B2 | 3/2011 | Popov et al. |
| 7,910,875 B2 | 3/2011 | Al-Ali |
| 7,919,713 B2 | 3/2011 | Al-Ali et al. |
| 7,937,128 B2 | 4/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 5/2011 | Lamego et al. |
| 7,962,188 B2 | 6/2011 | Kiani et al. |
| 7,962,190 B1 | 6/2011 | Diab et al. |
| 7,976,472 B2 | 6/2011 | Kiani |
| 7,988,637 B2 | 7/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| 8,019,400 B2 | 8/2011 | Diab et al. |
| RE42,753 E | 9/2011 | Kiani-Azarbayjany et al. |
| 8,028,701 B2 | 9/2011 | Al-Ali et al. |
| 8,029,765 B2 | 10/2011 | Bellott et al. |
| 8,032,206 B1 | 10/2011 | Farazi et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 7,904,132 B2 | 11/2011 | Weber et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |

(56) References Cited

U.S. PATENT DOCUMENTS

| | | |
|---|---|---|
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 2004/0267103 A1 | 12/2004 | Li et al. |
| 2007/0282478 A1 | 12/2007 | Al-Ali et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0299157 A1 | 12/2009 | Telfort et al. |
| 2010/0004518 A1 | 1/2010 | Vo et al. |
| 2010/0030040 A1 | 2/2010 | Poeze et al. |
| 2010/0069725 A1 | 3/2010 | Al-Ali |
| 2010/0261979 A1 | 10/2010 | Kiani |
| 2010/0317936 A1 | 12/2010 | Al-Ali et al. |
| 2011/0001605 A1 | 1/2011 | Kiani et al. |
| 2011/0082711 A1 | 4/2011 | Poeze et al. |
| 2011/0087083 A1 | 4/2011 | Poeze et al. |
| 2011/0105854 A1 | 5/2011 | Kiani et al. |
| 2011/0125060 A1 | 5/2011 | Telfort et al. |
| 2011/0172967 A1 | 7/2011 | Al-Ali et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0288383 A1 | 11/2011 | Diab |
| 2011/0301444 A1 | 12/2011 | Al-Ali |
| 2012/0041316 A1 | 2/2012 | Al-Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0116175 A1 | 5/2012 | Al-Ali et al. |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0302894 A1 | 11/2012 | Diab et al. |
| 2012/0319816 A1 | 12/2012 | Al-Ali |
| 2012/0330112 A1 | 12/2012 | Lamego et al. |

(56) References Cited

U.S. PATENT DOCUMENTS

| | | |
|---|---|---|
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0190581 A1 | 7/2013 | Al-Ali et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0262730 A1 | 10/2013 | Al-Ali et al. |
| 2013/0267804 A1 | 10/2013 | Al-Ali |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2014/0012100 A1 | 1/2014 | Al-Ali et al. |
| 2014/0034353 A1 | 2/2014 | Al-Ali et al. |
| 2014/0051953 A1 | 2/2014 | Lamego et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0127137 A1 | 5/2014 | Bellott et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0194766 A1 | 7/2014 | Al-Ali et al. |
| 2014/0206963 A1 | 7/2014 | Al-Ali |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0303520 A1 | 10/2014 | Telfort et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0336481 A1 | 11/2014 | Shakespeare et al. |
| 2014/0355966 A1 | 12/2014 | Al-Ali et al. |
| 2014/0371548 A1 | 12/2014 | Al-Ali et al. |
| 2014/0371632 A1 | 12/2014 | Al-Ali et al. |
| 2014/0378784 A1 | 12/2014 | Kiani et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0140863 A1 | 5/2015 | Al-Ali et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0201874 A1 | 7/2015 | Diab |
| 2015/0208966 A1 | 7/2015 | Al-Ali |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0029933 A1 | 2/2016 | Al-Ali et al. |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Kind et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0073967 A1 | 3/2016 | Lamego et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |

\* cited by examiner

PHYSIOLOGICAL PARAMETER SYSTEM

PRIORITY CLAIM TO RELATED PROVISIONAL APPLICATIONS

The present application is a continuation of U.S. patent application Ser. No. 14/507,415, filed Oct. 6, 2014, which is a continuation of U.S. patent application Ser. No. 11/963,640, filed Dec. 21, 2007, entitled "Physiological Parameter System," which claims priority benefit under 35 U.S.C. § 119(e) of U.S. Provisional Application Ser. No. 60/876,749, filed Dec. 22, 2006, entitled "Physiological Parameter System," which is incorporated herein by reference.

FIELD OF THE DISCLOSURE

The present disclosure relates to a sensor for measuring physiological parameters and, in particular, relates to using measured physiological parameters to generate an indicator.

BACKGROUND

Pulse oximetry is a widely accepted noninvasive procedure for measuring the oxygen saturation level of arterial blood, an indicator of a person's oxygen supply. Early detection of a low blood oxygen level is critical in the medical field, for example in critical care and surgical applications, because an insufficient supply of oxygen can result in brain damage and death in a matter of minutes. A typical pulse oximetry system utilizes a sensor applied to a patient's finger. The sensor has an emitter configured with both red and infrared LEDs that project light through the finger to a detector so as to determine the ratio of oxygenated and deoxygenated hemoglobin light absorption. In particular, the detector generates first and second intensity signals responsive to the red and IR wavelengths emitted by the LEDs after absorption by constituents of pulsatile blood flowing within a fleshy medium, such as a finger tip. A pulse oximetry sensor is described in U.S. Pat. No. 6,088,607 titled Low Noise Optical Probe, which is assigned to Masimo Corporation, Irvine, Calif. and incorporated by reference herein.

Capnography comprises the continuous analysis and recording of carbon dioxide concentrations in the respiratory gases of patients. The device used to measure the $CO_2$ concentrations is referred to as a capnometer. $CO_2$ monitoring can be performed on both intubated and non-intubated patients. With non-intubated patients, a nasal cannula is used. Capnography helps to identify situations that can lead to hypoxia if uncorrected. Moreover, it also helps in the swift differential diagnosis of hypoxia before hypoxia can lead to irreversible brain damage. Pulse oximetry is a direct monitor of the oxygenation status of a patient. Capnography, on the other hand, is an indirect monitor that helps in the differential diagnosis of hypoxia so as to enable remedial measures to be taken expeditiously before hypoxia results in an irreversible brain damage.

Early detection of low blood oxygen is critical in a wide variety of medical applications. For example, when a patient receives an insufficient supply of oxygen in critical care and surgical applications, brain damage and death can result in just a matter of minutes. Because of this danger, the medical industry developed pulse oximetry, a noninvasive procedure for measuring the oxygen saturation of the blood. A pulse oximeter interprets signals from a sensor attached to a patient in order to determine that patient's blood oxygen saturation.

A conventional pulse oximetry sensor has a red emitter, an infrared emitter, and a photodiode detector. The sensor is typically attached to a patient's finger, earlobe, or foot. For a finger, the sensor is configured so that the emitters project light from one side of the finger, through the outer tissue of the finger, and into the blood vessels and capillaries contained inside. The photodiode is positioned at the opposite side of the finger to detect the emitted light as it emerges from the outer tissues of the finger. The photodiode generates a signal based on the emitted light and relays that signal to the pulse oximeter. The pulse oximeter determines blood oxygen saturation by computing the differential absorption by the arterial blood of the two wavelengths (red and infrared) emitted by the sensor.

SUMMARY

Multiple physiological parameters, combined, provide a more powerful patient condition assessment tool than when any physiological parameter is used by itself. For example, a combination of parameters can provide greater confidence if an alarm condition is occurring. More importantly, such a combination can be used to give an early warning of a slowly deteriorating patient condition as compared to any single parameter threshold, which may not indicate such a condition for many minutes. Conditions such as hypovolemia, hypotension, and airway obstruction may develop slowly over time. A physiological parameter system that combines multiple parameters so as to provide an early warning could have a major effect on the morbidity and mortality outcome in such cases. Parameters can include ECG, EKG, blood pressure, temperature, $SpO_2$, pulse rate, HbCO, HbMet, Hbt, SpaO2, HbO2, Hb, blood glucose, water, the presence or absence of therapeutic drugs (aspirin, dapson, nitrates, or the like) or abusive drugs (methamphetamine, alcohol, or the like), concentrations of carbon dioxide ("CO2"), oxygen ("O"), ph levels, bilirubin, perfusion quality, signal quality, albumin, cyanmethemoglobin, and sulfhemoglobin ("HbSulf") respiratory rate, inspiratory time, expiratory time, inspiratory to expiratory ratio, inspiratory flow, expiratory flow, tidal volume, minute volume, apnea duration, breath sounds—including rales, rhonchi, or stridor, changes in breath sounds, heart rate, heart sounds—including S1, S2, S3, S4, or murmurs, or changes in heart sounds, or the like. Some references that have common shorthand designations are referenced through such shorthand designations. For example, as used herein, HbCO designates carboxyhemoglobin, HbMet designates Methemoglobin, and Hbt designates total hemoglobin. Other shorthand designations such as COHb, MetHb, and tHb are also common in the art for these same constituents. These constituents are generally reported in terms of a percentage, often referred to as saturation, relative concentration or fractional saturation. Total hemoglobin is generally reported as a concentration in g/dL. The use of the particular shorthand designators presented in this application does not restrict the term to any particular manner in which the designated constituent is reported.

Further, a greater emphasis has been put on decreasing the pain level of patients on the ward. Accordingly, patients are often given an IV setup that enables the patient to increase the level of analgesia at will. In certain situations, however, the patient's input must be ignored so as to avoid over medication. Complications from over sedation may include hypotension, tachycardia, bradycardia, hypoventilation and apnea. A physiological parameter system that uses pulse oximetry monitoring of $SpO_2$ and pulse rate in conjunction with patient controlled analgesia (PCA) can aid in patient safety. Utilization of conventional pulse oximetry in conjunction with PCA, however, can result in the patient being erroneously denied pain medication. Conventional monitors are susceptible to patient motion, which is likely to increase with rising pain. Further, conventional monitors do not provide an indication of output reliability.

Advanced pulse oximetry is motion tolerant and also provides one or more indications of signal quality or data confidence. These indicators can be used as arbitrators in decision algorithms for adjusting the PCA administration and sedation monitoring. Further, advanced pulse oximetry can provide parameters in addition to oxygen saturation and pulse rate, such as perfusion index (PI). For example, hypotension can be assessed by changes in PI, which may be associated with changes in pulse rate. Motion tolerant pulse oximetry is described in U.S. Pat. No. 6,206,830 titled Signal Processing Apparatus and Method; signal quality and data confidence indicators are described in U.S. Pat. No. 6,684,090 titled Pulse Oximetry Data Confidence Indicator, both of which are assigned to Masimo Corporation, Irvine, Calif. and incorporated by reference herein.

One aspect of a physiological parameter system is a first parameter input responsive to a first physiological sensor and a second parameter input responsive to a second physiological sensor. A processor is adapted to combine the parameters and predetermined limits for the parameters so as to generate an indication of wellness.

Another aspect of a physiological parameter system is a parameter input responsive to a physiological sensor and a quality indicator input relating to confidence in the parameter input. A processor is adapted to combine the parameter input, the quality indicator input and predetermined limits for the parameter input and the quality indicator input so as to generate a control output.

A physiological parameter method comprises the steps of inputting a parameter responsive to a physiological sensor and inputting a quality indicator related to data confidence for the parameter. A control signal is output from the combination of the parameter and the quality indicator. The control signal is adapted to affect the operation of a medical-related device.

A method of improving the reporting of a physiological parameter in a physiological parameter system comprises obtaining measurements of a physiological parameter from a measurement site. At least some of the physiological parameter measurements are maintained. A change in the measurement site is detected. A measurement of the physiological parameter from a new measurement site is obtained. The measurement of the physiological parameter at the new measurement site is compared with the maintained physiological parameter measurements. The magnitude of the physiological parameter reported by the physiological parameter system at the new measurement site is adjusted to approximately match the magnitude of the maintained physiological parameter measurements.

A method of generating an indicator of patient wellness using a physiological parameter system includes receiving physiological parameter data from a sensor attached to the physiological parameter system. Physiological parameter preferences are provided to the physiological parameter system. The physiological parameter data is compared to the physiological parameter preferences. An indicator of patient wellness is generated by calculating a numerical wellness score based on the comparison.

DETAILED DESCRIPTION OF PREFERRED EMBODIMENTS

Hereinafter, various example embodiments of the present disclosure will be described in detail with reference to the attached drawings such that the present disclosure can be put into practice by those skilled in the art. However, the present disclosure is not limited to the example embodiments, but may be embodied in various forms.

Some embodiments will be described in the context of computer-executable instructions, such as program modules, being executed by hardware devices, such as embedded processors, microcontrollers, and computer workstations. Program modules may include routines, programs, objects, components, data structures, etc. that perform particular tasks or implement particular data types. Computer-executable instructions, associated data structures, and program modules represent examples of program code for executing steps of the methods disclosed herein. The particular sequence of executable instructions or arrangement of associated data structures represents examples of corresponding acts for implementing the functions described in such steps. A person of skill in the art would understand that other structures, arrangements, and executable instructions could be used with the present disclosure without departing from the spirit thereof.

Figure 1:
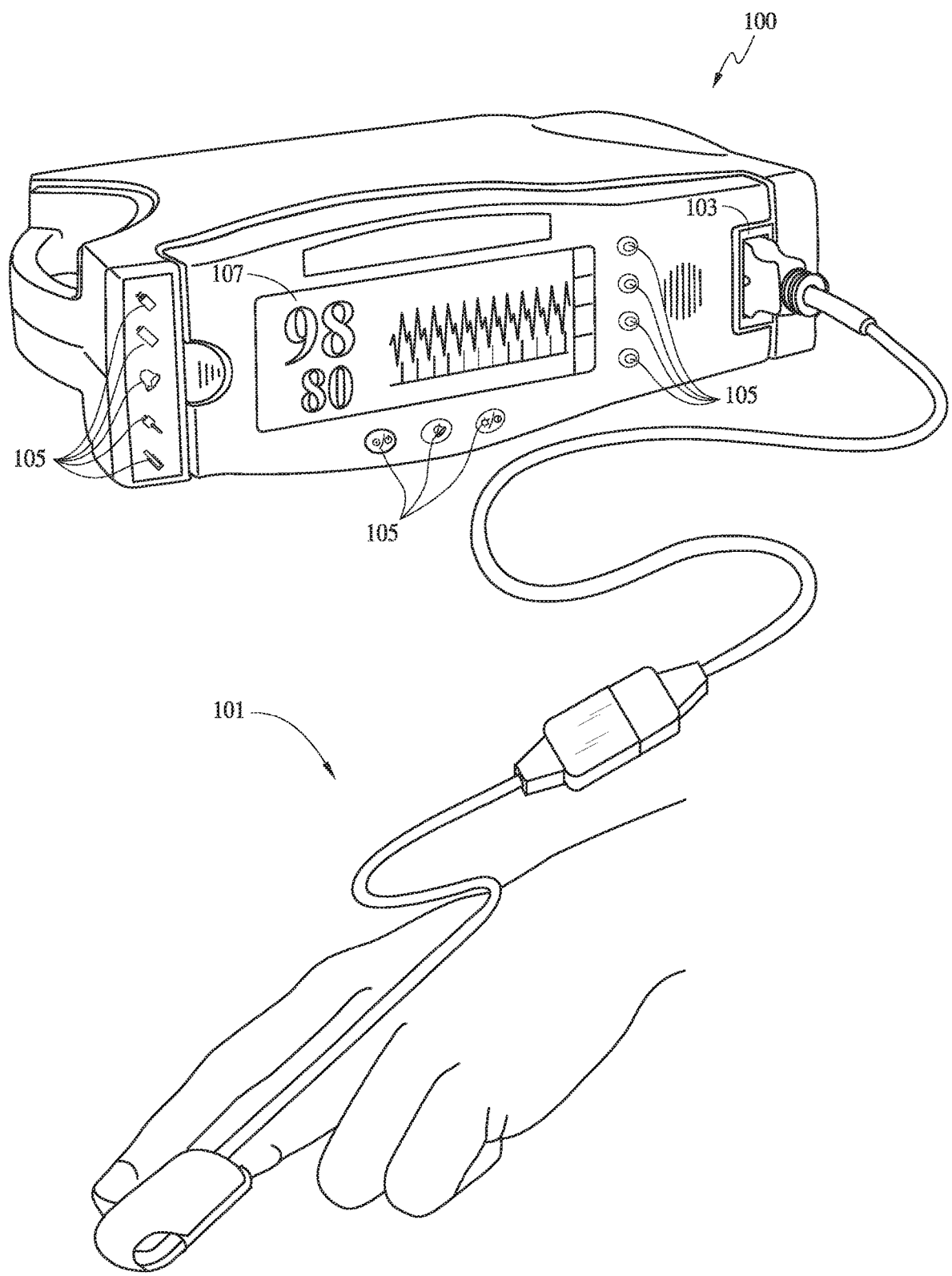
FIG. 1 illustrates an embodiment of a physiological parameter measurement system.

FIG. 1 illustrates an embodiment of a physiological measurement system 100 having a monitor 101 and a sensor assembly 101. The physiological measurement system 100 allows the monitoring of a person, including a patient. In particular, the multiple wavelength sensor assembly 101 allows the measurement of blood constituents and related parameters, including oxygen saturation, COHb, MetHb and pulse rate.

In an embodiment, the sensor assembly 101 is configured to plug into a monitor sensor port 103. Monitor keys 105 provide control over operating modes and alarms, to name a few. A display 107 provides readouts of measured parameters, such as oxygen saturation, pulse rate, COHb and MetHb to name a few.

Figure 2A:
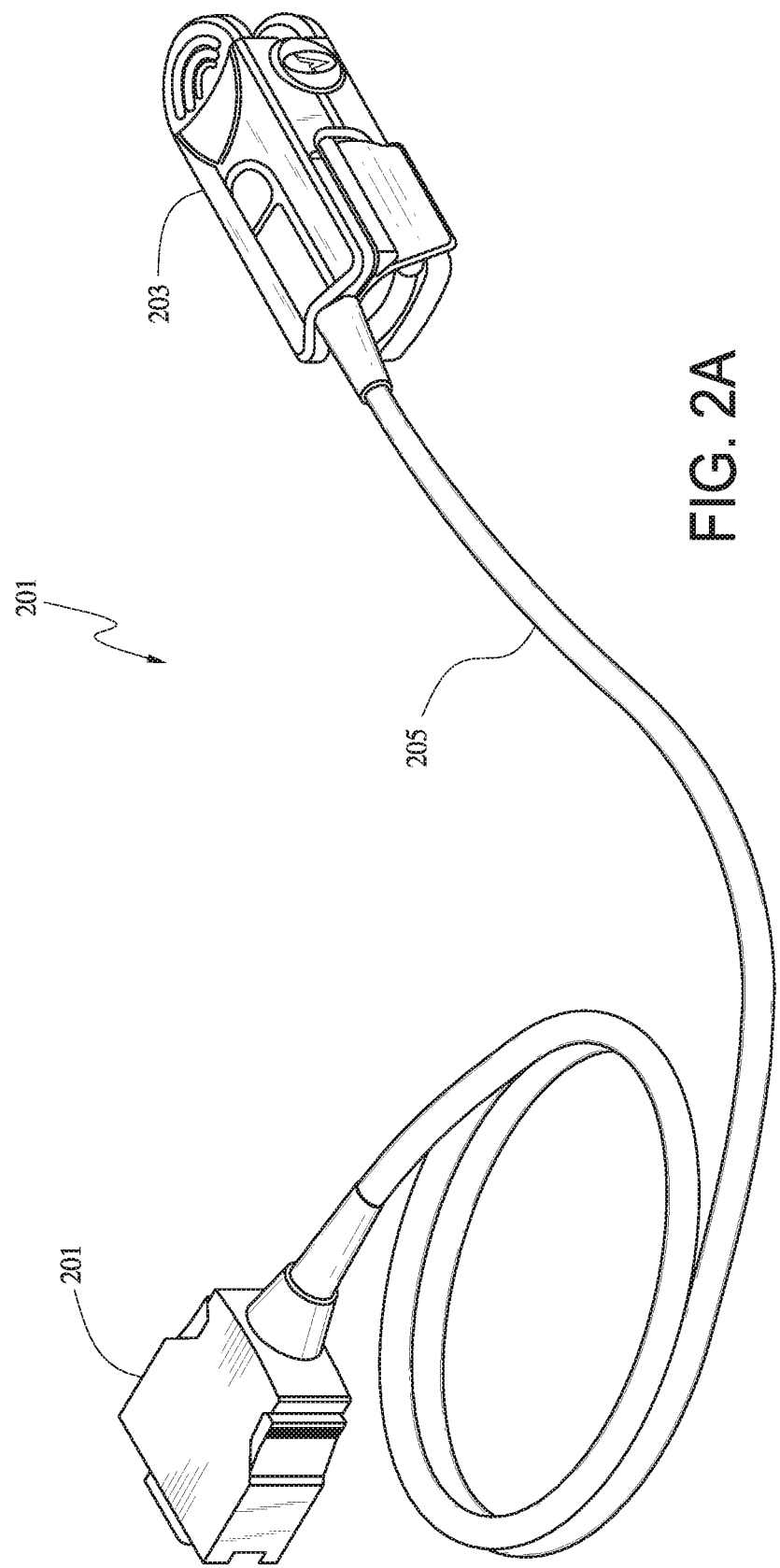
FIG. 2A illustrates an embodiment of a sensor assembly.

FIG. 2A illustrates a multiple wavelength sensor assembly 201 having a sensor 203 adapted to attach to a tissue site, a sensor cable 205 and a monitor connector 201. In an embodiment, the sensor 203 is incorporated into a reusable finger clip adapted to removably attach to, and transmit light through, a fingertip. The sensor cable 205 and monitor connector 201 are integral to the sensor 203, as shown. In alternative embodiments, the sensor 203 can be configured separately from the cable 205 and connector 201, although such communication can advantageously be wireless, over public or private networks or computing systems or devices, through intermediate medical or other devices, combinations of the same, or the like.

Figure 2B:
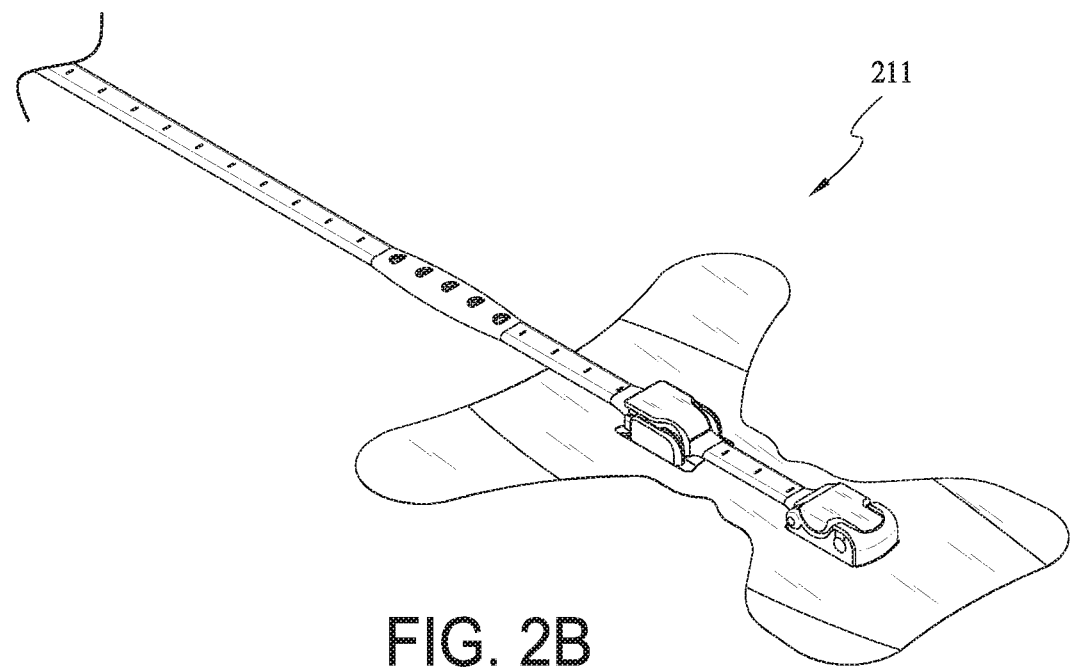
FIGS. 2B-C illustrate alternative sensor embodiments.
Figure 2C:
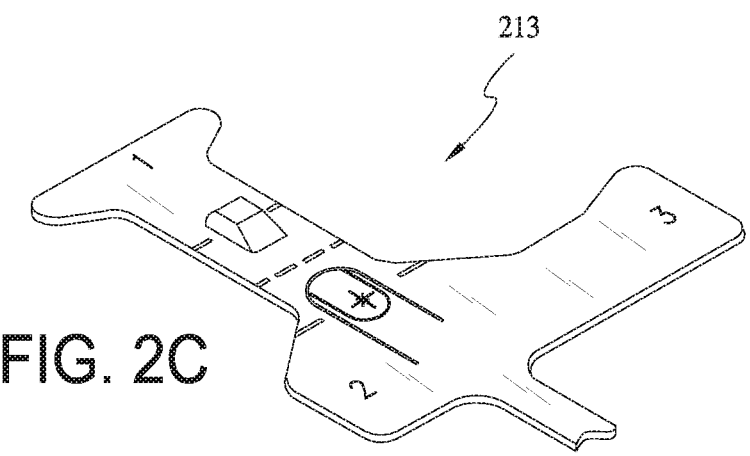

FIGS. 2B-C illustrate alternative sensor embodiments, including a sensor 211 (FIG. 2B) partially disposable and partially reusable (resposable) and utilizing an adhesive attachment mechanism. Also shown is a sensor 213 being disposable and utilizing an adhesive attachment mechanism. In other embodiments, a sensor can be configured to attach to various tissue sites other than a finger, such as a foot or an ear. Also a sensor can be configured as a reflectance or transflectance device that attaches to a forehead or other tissue surface. The artisan will recognize from the disclosure herein that the sensor can include mechanical structures, adhesive or other tape structures, Velcro wraps or combination structures specialized for the type of patient, type of monitoring, type of monitor, or the like.

Certain physiological parameters and certain changes in physiological parameters may serve as indicators of an adverse condition affecting a patient. For example, an increase in blood methemoglobin (MetHb) concentration may be useful as a marker of the onset of sepsis or septic shock. As another example, measurements of high blood carboxyhemoglobin (COHb) concentration may indicate exposure to carbon monoxide (CO). Other physiological and related parameters to which techniques of the present disclosure may be applicable include respiration rate, respiration volume, oxygen saturation, pulse rate, ECG, blood glucose, blood pressure, temperature, perfusion index, exhaled carbon dioxide waveform, end tidal carbon dioxide, various signal quality indicators, data confidence indicators and trend data, among others.

A sensor measuring a physiological parameter (e.g., a physiological parameter measurement device) of a patient may, under certain circumstances, detect a change in the magnitude of a detected signal that does not correspond to a change in the value of the physiological parameter. Such changes in a detected signal may occur, for example, when the sensor is moved to a different measurement site. Sometimes, a sensor may be temporarily removed from a patient, and medical reasons may compel movement of the sensor to a different location. For example, a multiple wavelength sensor may need to be moved to a different finger of a patient about every 12 hours in order to maintain the sensor's measurement effectiveness and/or to avoid injury to the patient. When the measurement site of a multiple wavelength sensor is switched to a different location, the magnitudes of some of the signals detected by the sensor may change, even though no significant change in the patient's physiological parameters has occurred during the brief sensor relocation period. Signal normalization techniques described in the present disclosure may reduce changes in physiological parameters reported by a physiological parameter system that are unrelated to actual physiological parameter variation.

In some cases, the magnitude of a sensor measurement may be a less effective indicator of an adverse condition than a change in the magnitude of a sensor measurement. In such cases, a sensor may not need to be calibrated to report the absolute magnitude of a physiological parameter when changes in the magnitude of the parameter are more significant for purposes of condition detection. In other cases, the absolute magnitude of a physiological parameter is valuable, and a sensor signal must be analyzed and/or recalibrated to compensate for changes in the magnitude of the signal detected that do not correspond to changes in the value of the physiological parameter being measured. Signal normalization techniques may improve a physiological parameter system's reporting effectiveness for both types of parameters.

Figure 3A:
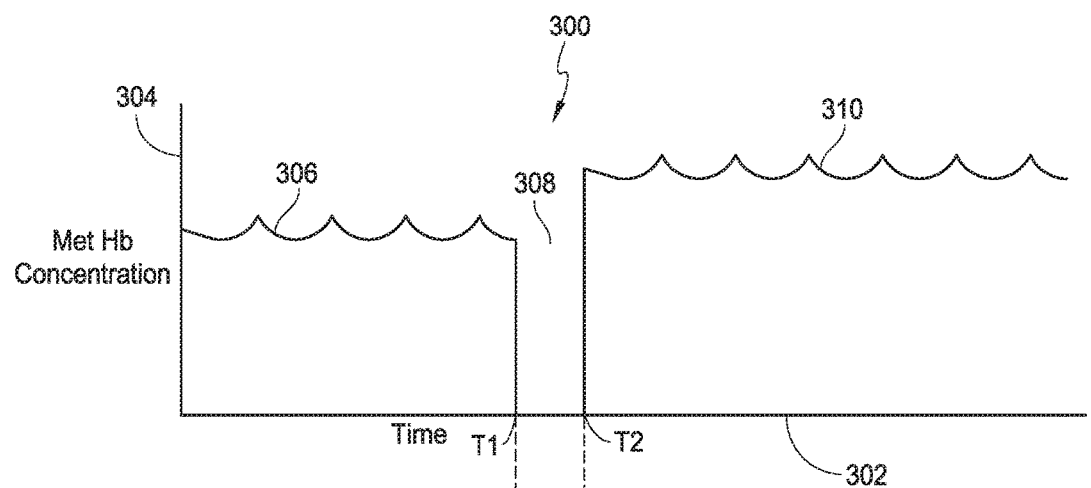
FIG. 3A illustrates an example chart of the value of a physiological parameter as measured by a sensor during a time when the sensor is moved from one measurement site to another.

FIG. 3A illustrates an example chart 300 of the value of a physiological parameter, such as, for example, MetHb, as measured by a sensor during a time when the sensor is moved from one measurement site to another. Chart 300 shows the magnitude of a signal measured by a sensor as a function of time before any analysis or manipulation of the signal occurs. A first axis 302 of chart 300 represents time, and a second axis 304 represents the magnitude of a signal, corresponding to a physiological parameter, detected at a point in time. The physiological parameter corresponding to the signal shown by way of example in FIG. 3A is blood MetHb concentration.

Curve 306 represents the magnitude of the signal detected by a sensor during a period when the sensor was at a first measurement site. The signal represented by curve 306 roughly oscillates about a nearly constant mean value of the signal. However, the signal may also follow any continuous increasing or decreasing trend and may also be nonoscillatory or contain a complex pattern of variation.

At time T1 along axis 302, the sensor is removed from the first measurement site. Curve 308 represents the magnitude of the signal detected by the sensor while it is disconnected from the patient, for example, while a care provider switches the sensor to a new measurement site. In chart 300, the magnitude of the signal is about zero, but the sensor may continue to detect a signal of some nature (e.g., random noise, background interference, etc.) during a period when it is disconnected from a patient.

At time T2 along axis 302, the sensor is attached to a second measurement site on the patient. The second measurement site may be different than the first measurement site; for example, the second measurement site may be a different finger or a different position on a finger. Curve 310 represents the magnitude of the signal detected by the sensor during a period when the sensor is at the second measurement site. The signal represented by curve 310 roughly oscillates about a nearly constant mean value of the signal that is higher than the mean value of the portion of the signal represented by curve 306. The difference between the magnitude of the signal shortly before time T1 and the magnitude of the signal shortly after time T2 is a shift in the magnitude of the signal that is related to the change in the measurement site. However, the shift in the signal may not correspond to an actual change in the value of a physiological parameter of the patient. In some cases, it may be safe to assume that the approximate value of a physiological parameter shortly before time T1 and shortly after time T2 is the same. In the absence of signal normalization, the signal shift may trigger a false alarm or cause a physiological parameter system to incorrectly report a change in a parameter. In the embodiment shown in FIG. 3A, reporting the non-normalized signal may trigger an alarm for sepsis or septic shock at time T2 due to an apparent increase in blood MetHb concentration.

Figure 3B:
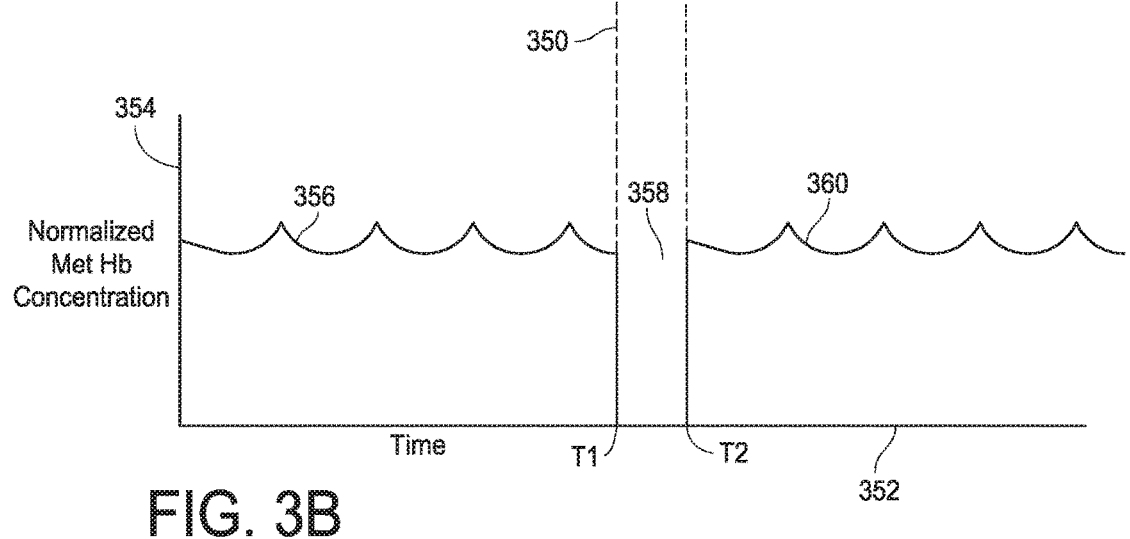
FIG. 3B illustrates a chart of a physiological parameter reported by a measurement system employing signal normalization techniques.

FIG. 3B illustrates a chart 350 of a physiological parameter reported by a measurement system employing signal normalization techniques. In the situation corresponding to chart 350, it is assumed that the approximate value of the physiological parameter shortly before time T1 is the same as the approximate value of the physiological parameter shortly after time T2. A first axis 352 of chart 350 represents time, and a second axis 354 represents the value of a physiological parameter reported by a physiological parameter system at a point in time. The physiological parameter shown by way of example in FIG. 3B is blood MetHb concentration.

In chart 350, curve 356 represents the value of the physiological parameter reported while the sensor is at the first measurement site. Curve 358 represents the value of the physiological parameter reported while the sensor is not connected to the patient. In alternative embodiments, a physiological parameter system may not report a parameter or may shut off the sensor when the system detects that the sensor is not at a measurement site. Curve 360 represents the value of the physiological parameter reported while the sensor is at the second measurement site. The physiological parameter data in chart 350 is normalized because the value of the physiological parameter reported just before T1 is adjusted to match the value of the physiological parameter just after T2. Various methods of matching may exist, including adjusting the values before and after the measurement site change to be approximately equal, using data points before T1 to generate a trend line and fixing the data point at T2 to the trend line, or any other method known in the art of projecting or approximating the value of the physiological parameter at T2 based on data prior to T1.

In some embodiments, sensor measurements that are received after time T2, as shown in curve 310 of chart 300 (FIG. 3A), may be normalized by adding an offset to the magnitudes of the measurements. The offset may be calculated by subtracting the magnitude of the non-normalized sensor measurement at time T2 from the magnitude of the normalized sensor measurement at T2. The offset may be a negative number. Similar methods of normalizing data points involving, for example, subtraction of an offset and other known methods may also be used. One result of signal normalization is that, given a relatively constant physiological parameter over time, the mean value of curve 360 will more closely approximate the mean value of curve 356. Signal normalization may reduce the incidence of false alarms and reports of changes in physiological parameters that have not in fact changed.

Figure 3C:
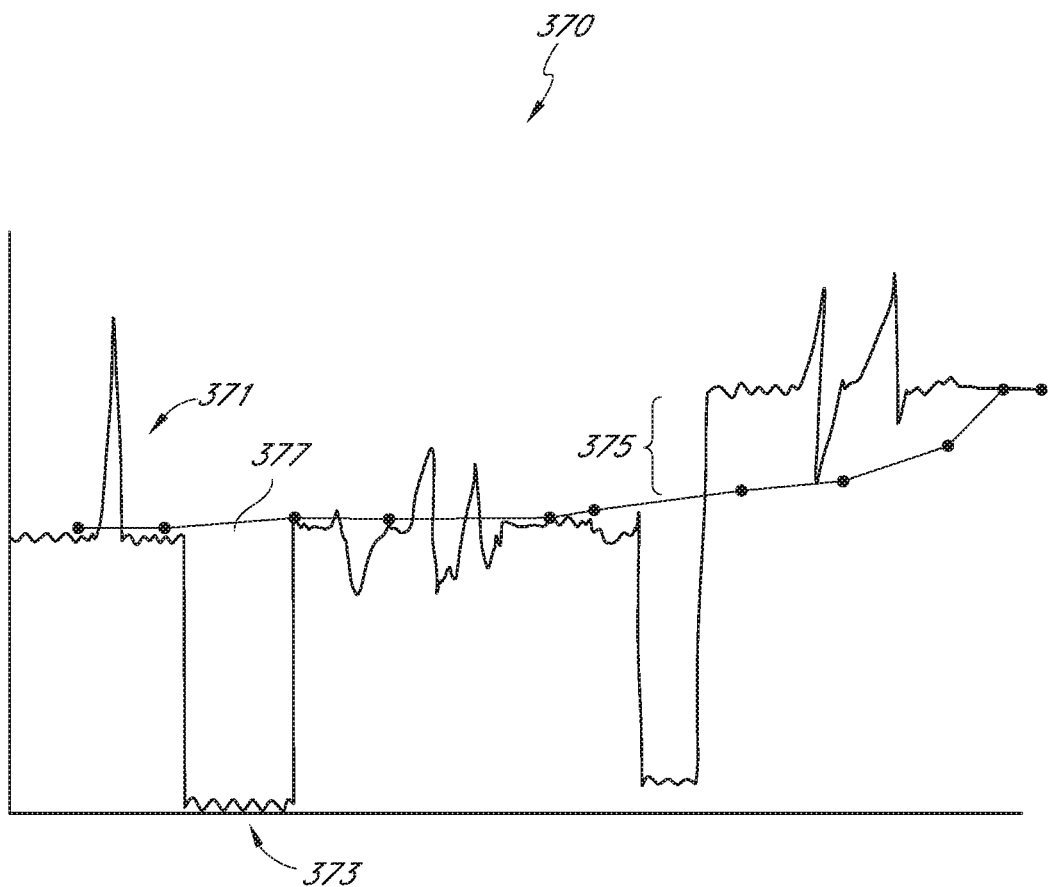
FIG. 3C illustrates a chart of a MetHb reading which is smoothed to account for abnormal variations in the readings.

FIG. 3C illustrates a further example of normalizing a signal with erratic noise, such as, for example, motion induced noise. As illustrated, a physiological parameter signal 370, such as a signal indicative of MetHb, is illustrated. The physiological parameter signal 370 includes various inconsistencies, such as, for example, erratic noises 371, probe off conditions 373, and cite change conditions 375. In order to deal with these inconsistencies, processing is used to determine a normalization 377 or trend of the signal. The normalization 377 uses various methods in order to determine a relatively stable physiological parameter reading 377.

Figure 3D:
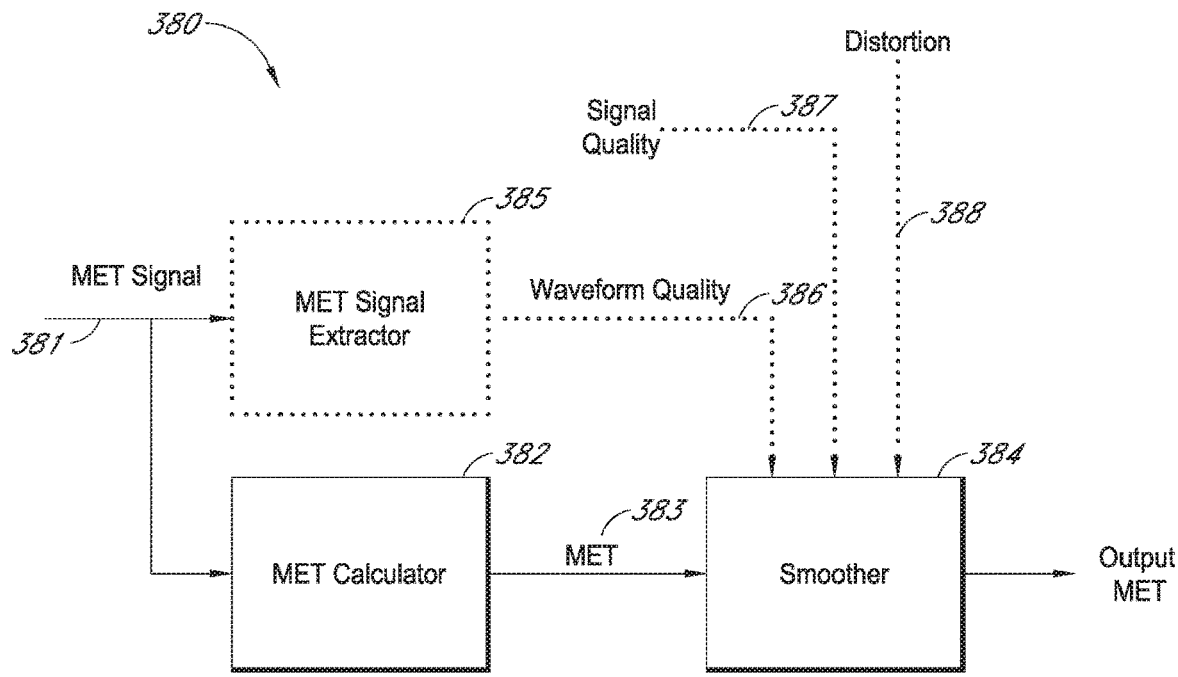
FIG. 3D illustrates a MetHb smoothing flowchart.

FIG. 3D illustrates a flow chart of a normalization procedure 380. For ease in discussion, FIGS. 3D and 3E will be discussed with respect to a MetHb reading, however, it should be understood that any physiological parameter can be used with the present disclosure. The normalization procedure begins with the data signal 381. As show, the normalization feature 380 includes Met calculator 382; smoother 384, Met signal extractor 385; signal quality 387 and distortion 388. In an embodiment, a data signal 381 responsive to an intensity signal is input into the Met calculator 382, and a current value 383 of Met is calculated. The current value 383 of Met, which in an embodiment is subject to noise, distortion, and site movements in the data signal 381, is input into the smoother 384, which reduces an error between the current value 383 of Met and actual MetHb conditions. For example, the smoother 384 may advantageously determine a Met trend, and depending upon an indication of some or all of an amount of distortion, noise, signal quality, and/or waveform quality in the data signal 383, substitute or combine the MetHb trend for or with the current value 383 to generate an output MetHb measurement.

In an embodiment, the distortion signal 388 may comprise a Boolean value indicating whether the data signal 383 includes, for example, motion-induced noise. Although an artisan will recognize from the disclosure herein a number of methodologies for deriving the distortion signal 388, derivation of a Boolean distortion signal is disclosed in U.S. Pat. No. 6,606,511, incorporated herein by reference. Alternatively, or in addition to, the signal quality signal 387 may comprise a Boolean value indicating whether the data signal 383 meets various waveform criteria Although an artisan will recognize from the disclosure herein a number of methodologies for deriving the signal quality signal 387, derivation of a Boolean distortion signal is disclosed in the '511 patent. Alternatively, or in addition to, a feature extractor 385 may advantageously produce waveform quality outputs 386, indicative of waveform quality or waveform shape. Although an artisan will recognize from the disclosure herein a number of methodologies for deriving the waveform quality signal 386, derivation thereof is disclosed in U.S. Pat. No. 6,334,065, also incorporated herein by reference.

Thus, the smoother 384 accepts one or more or different indicators of the quality of the data signal 381, and determines how to smooth or normalize the output to reduce errors between data trends and actual MetHb conditions. In an embodiment, the smoothing may advantageously comprise statistical weighting, other statistical combinations, or simply passing the MetHb measurement 383 through to the output, depending upon one or more of the quality signals 386, 387, 388, or logical combinations thereof.

Upon the output of the normalized MetHb measurement, a monitor may advantageously audibly and/or visually presents the measurement to a caregiver, and when the measurement meets certain defined thresholds or behaviors, the monitor may advantageously audibly and/or visually alert the caregiver. In other embodiments, the monitor may communicate with other computing devices to alert the caregiver, may compare longer term trend data before alarming, or the like.

Figure 3E:
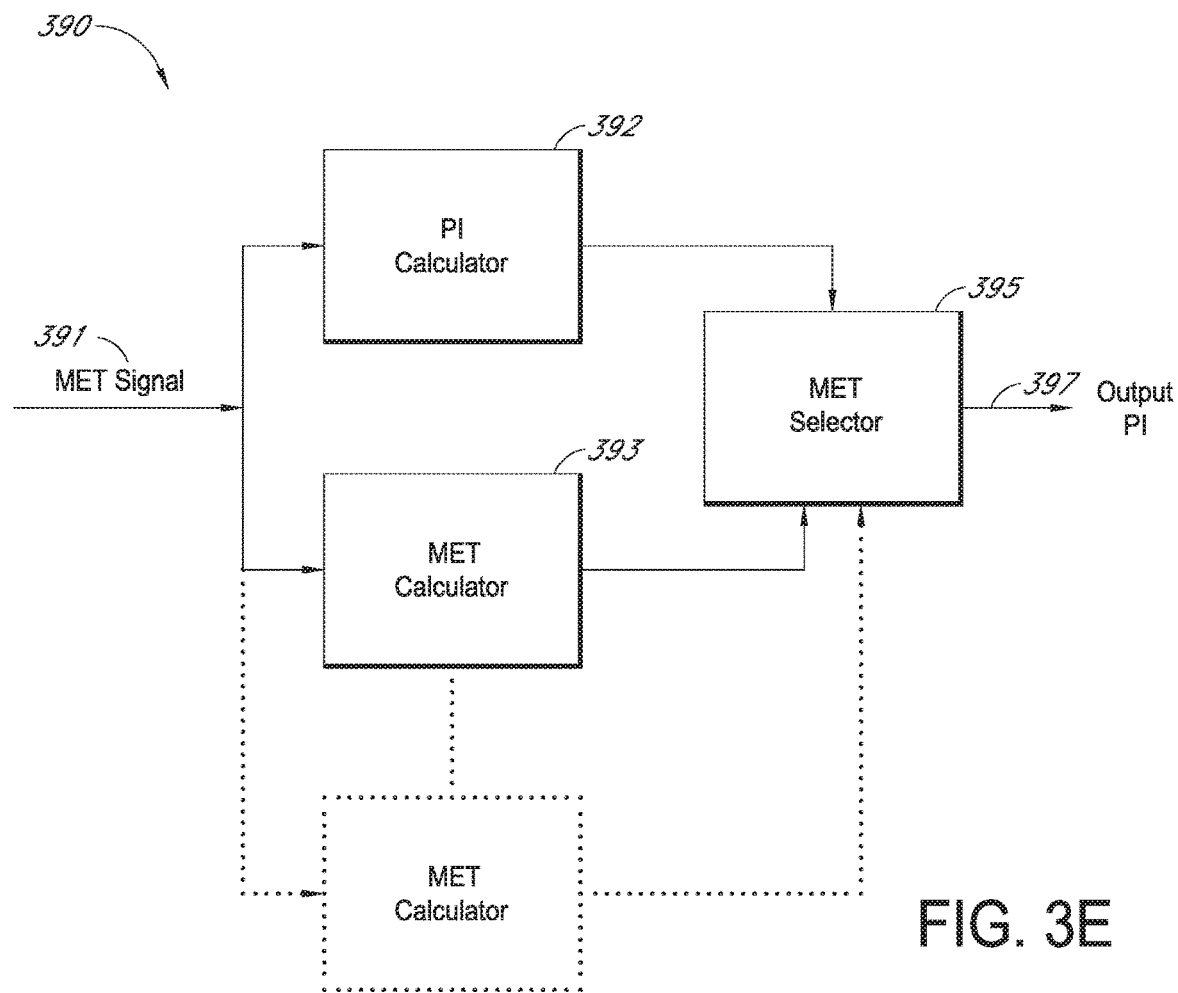
FIG. 3E illustrates a system of multiple different MetHb calculators which determine MetHb using different methods in order to calculate the most accurate MetHb reading.

FIG. 3E illustrates a simplified block diagram of an embodiment of a MetHb determination system 390 using multiple Met calculation techniques. As shown, data 391 is input into the system. The data 391 is then routed to at least two different Met calculators 392, 393. In an embodiment, more than two different types of calculation techniques can be used. The at least two Met calculators 392, 393 output Met indications for input into the Met selector 395. The Met selector 395 determines a Met value to output. The Met selector chooses the output based on which Met calculator works best for a given condition of the signal or based on which Met calculation fits the trend of Met readings. Other methods of selecting the best Met value can also be made as would be understood by a person of skill in the art from the present disclosure.

Figure 4:
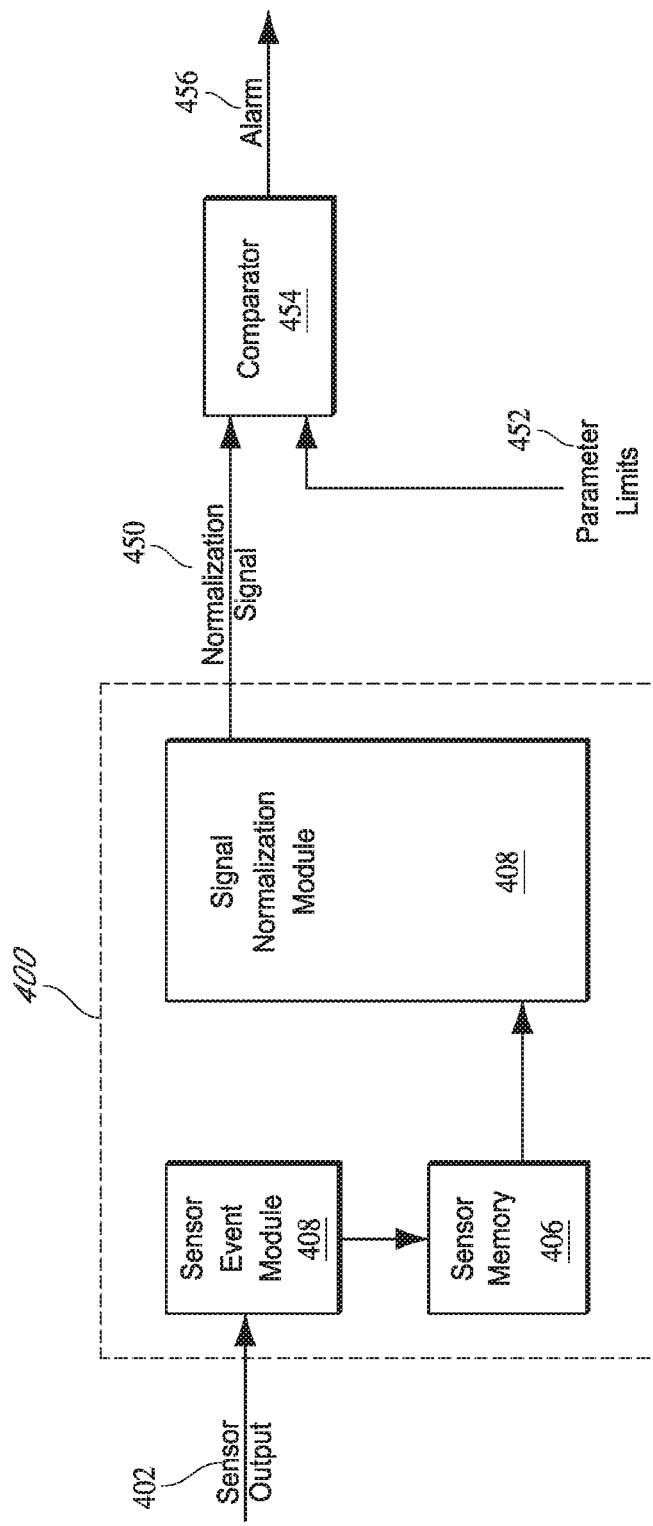
FIG. 4 is a block diagram of a physiological parameter system having signal normalization capability.

FIG. 4 is a block diagram of a physiological parameter system having signal normalization capability. A physiological parameter system may include a sensor signal analysis subsystem 400 that implements signal normalization techniques. Signal analysis subsystem 400 receives a signal 402 from a physiological parameter measurement device output. Signal 402 may be, for example, an electrical signal produced by an optical transducer within a pulse oximeter or a capnometer.

In the embodiment shown in FIG. 4, signal 402 is communicated to a sensor event module 404. Sensor event module 404 includes program code for detecting events that occur based on a pattern recognized in signal 402. Detected events may include a change in measurement site, movement of the sensor, interference in the signal, etc. For example, sensor event module 404 may determine that a measurement site of the sensor has been exchanged if a normal physiological parameter pattern ceases for a short period of time and then resumes. Alternatively, sensor event module 404 may detect a measurement site switch when signal 402 is interrupted by an interval of random noise and/or a relatively large discontinuity in the signal. Alternatively, an operator can indicate an event, such as a location change, by, for example, pressing a predetermined function button. As another example, sensor event module 404 may determine that signal normalization may not be appropriate when a sensor has been disconnected from a measurement site for a sufficiently long period of time (e.g., when an assumption that a signal trend will continue is no longer sound). Sensor event module 404 may communicate signal 402 and/or event information to a sensor memory 406 to store sensor signal pattern data for later use. Sensor event module 404 may also communicate signal 402 and event information to signal normalization module 408.

Sensor memory 406 may retain a certain number of signal 402 samples or may retain signal 402 samples for a certain period. Retained samples may be used by program code in signal normalization module 408 and/or sensor event module 404. Samples from signal 402 may be stored in a queue data structure, for example. In some embodiments, sensor event module 404 may instruct sensory memory 406 to cease storing new samples when it determines that the sensor is not connected to a measurement site so that signal data for potential future signal normalization may be retained. Signal memory 406 may also retain signal offset or calibration data.

Signal normalization module 408 comprises program code for converting a signal 402 from a sensor output into a normalized measure of a physiological parameter. Program code in module 408 may, for example, add or subtract a value from signal 402 in order to eliminate shifts in the magnitude of signal 402 that are not related to variation in a patient's physiological parameters. Signal normalization module 408 may determine an offset that counterbalances a shift in signal 402 that results from a change in sensor measurement site. Module 408 may include program code for calculating a trend line from data stored in sensor memory 406. A trend line may be used to determine an appropriate value for a patient parameter when measurement resumes after an interruption in signal 402. Module 408 may also employ pattern recognition or signal transforms to help it determine how signal 402 should be normalized. Sensor event module 404 may trigger signal normalization module 408 to reset its signal normalization when a certain signal events are detected. In some embodiments, sensor event module 404 may communicate to signal normalization module 408 the retained signal data from sensor memory 406 it should use to calculate a new offset. Signal normalization module 408 passes a normalized signal 450 out of signal normalization subsystem 400.

Normalized signal 450 may then be passed to other components of a physiological parameter system for further analysis and/or display. For example, normalized signal 450 may be communicated to a comparator 454 that compares signal 450 to one or more parameter limits 452. In some embodiments, comparator 454 may generate an alarm signal 456 if normalized signal 450 falls outside of parameter limits 452.

Figure 5:
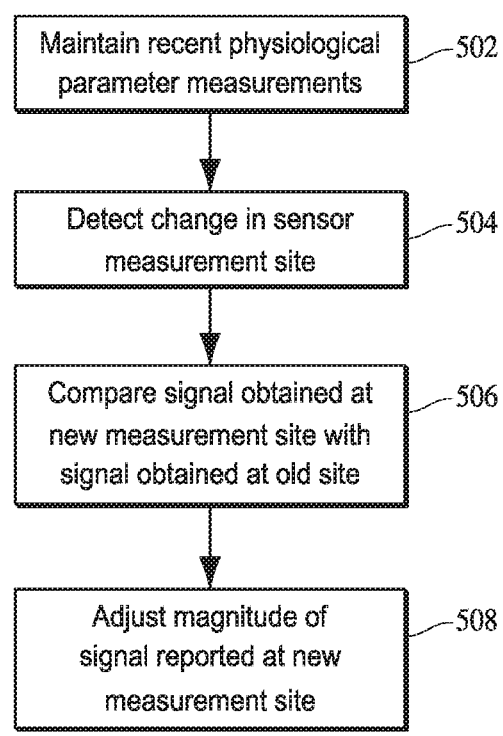
FIG. 5 illustrates an embodiment of a method for normalizing a signal acquired by a sensor.

FIG. 5 illustrates an embodiment of a method for normalizing a signal acquired by a sensor when the measurement site of the sensor is changed. At step 502, sensor memory 406 (FIG. 4) maintains recent physiological parameter measurements received from sensor output 402. Sensor signal data may be passed directly to sensor memory 406 for storage, or sensor event module 404, for example, may select which signal samples will be retained and pass them to sensor memory 406. Retained signal sample data may include the magnitude of the signal as well as an indicator of the time that the sample was taken and/or the order in which the sample was received. Alternatively, sensor memory 406 may simply maintain signal data in chronological order in a queue, purging old sample data as new sample data is received. Data may be retained only for a certain time interval, such several seconds, a fraction of a minute, a minute, two minutes, or longer. The interval of retention may vary depending on the physiological parameter associated with signal 402. This step may continue until sensor event module 404 detects a sensor measurement site change.

In step 504 of FIG. 5, sensor event module 404 detects a change in the sensor measurement site. In some embodiments, sensor event module 404 may detect the change in measurement site by one of the methods described with respect to the description of program code within sensor event module 404 above. Alternatively, a user of a physiological parameter system may indicate that a change in sensor measurement site has occurred by means of a hardware or software interface. For example, the sensor may include a hardware switch that activates when the measurement site is changed. The system may also include a manual switch or button that a user can activate to cause sensor event module 404 to register a change in the sensor measurement site. When sensor event module 404 determines that sampling at the new measurement site has begun, the method proceeds to step 506.

At step 506, signal normalization module 408 compares the magnitude of the signal sampled at the new measurement site with the magnitude of the retained signal that was obtained at the old measurement site. Signal normalization module 408 may use pattern recognition or signal transform techniques to attempt to compare an oscillatory signal at similar points in its cycle to obtain a more accurate comparison. In some embodiments, module 408 uses the comparison to calculate an offset that adjusts the signal at the time that measurement at the new measurement site begins to conform to a trend line fitted to signal data acquired from the old measurement site. Retained signal data from the old measurement site may be retrieved from sensor memory 406 and analyzed for the purpose of calibrating the sensor signal at the new measurement site. After the initial physiological parameter value is projected when the sensor begins sampling at the new measurement site, the method proceeds to step 508.

In step 508, signal normalization module 408 adjusts the magnitude of the signal measured at the new measurement site in order to output a normalized signal 450. In some embodiments, adjusting the magnitude of the signal measured comprises modifying the magnitude of a signal measure measurement by adding or subtracting an offset. For example, the offset may be calculated by subtracting the magnitude of the signal sampled just after the sensor begins measurements at the new measurement site from the magnitude of the signal sampled just before the sensor was removed from the old measurement site. Alternatively, the offset may be defined as the difference between (1) a projected value of the magnitude of the signal just after the sensor begins measurements at the new measurement site, the projection based on measurements at the old measurement site, and (2) the actual measured value of the magnitude of the signal just after the sensor begins measurements at the new measurement site. Any other known means for calculating an offset may also be used. Signal normalization module 408 continues to add or subtract the calculated offset until another normalization step is required. At the conclusion of the method shown in FIG. 5, the steps shown may be repeated as many times as changes in the measurement site of the sensor may require.

Various embodiments of signal normalization techniques have been shown and described. Some alternative embodiments and combinations of embodiments disclosed herein have already been mentioned. Additional embodiments comprise various other combinations or alterations of the embodiments described.

Figure 6:
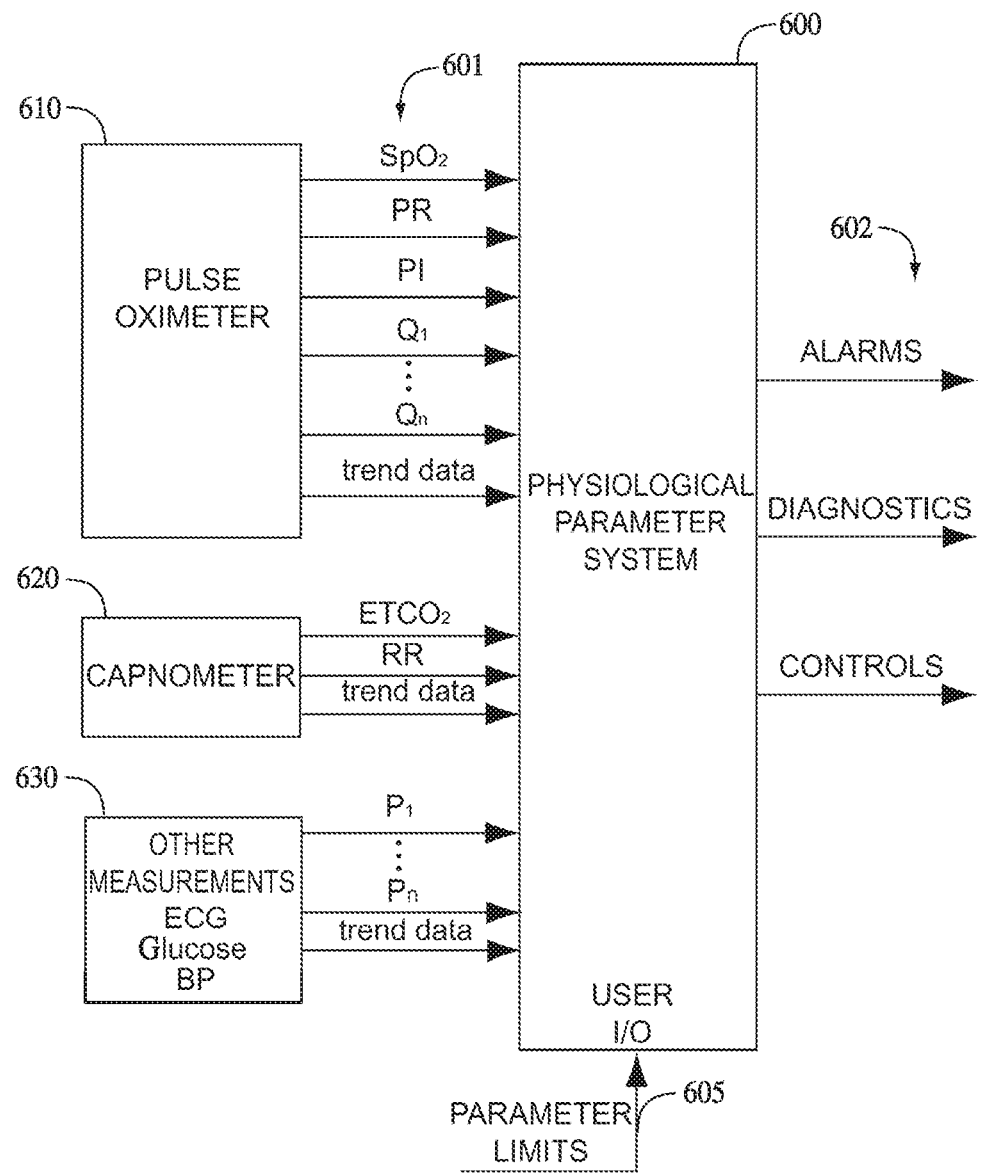
FIG. 6 is a general block diagram of a physiological parameter system having alarm, diagnostic and control outputs.

FIG. 6 illustrates a physiological parameter system 600, which may comprise an expert system, a neural-network or a logic circuit, for example. The physiological parameter system 600 has as inputs 601 from one or more parameters from one or more physiological measurement devices, such as a pulse oximeter 610 and/or a capnometer 620. Pulse oximeter parameters may include oxygen saturation ($SpO_2$), perfusion index (PI), pulse rate (PR), various signal quality and/or data confidence indicators (Qn) and trend data, to name a few. Capnography parameter inputs may include, for example, an exhaled carbon dioxide waveform, end tidal carbon dioxide ($ETCO_2$) and respiration rate (RR). Signal quality and data confidence indicators are described in U.S. Pat. No. 6,108,090 cited above. The physiological parameter system 600 may also have parameter limits 606, which may be user inputs, default conditions or otherwise predetermined thresholds within the system 600.

The inputs 601 are processed in combination to generate one or more outputs 602 comprising alarms, diagnostics and controls. Alarms may be used to alert medical personnel to a deteriorating condition in a patient under their care. Diagnostics may be used to assist medical personnel in determining a patient condition. Controls may be used to affect the operation of a medical-related device. Other measurement parameters 630 that can be input to the monitor may include or relate to one or more of ECG, blood glucose, blood pressure (BP), temperature (T), HbCO, MetHb, respiration rate and respiration volume, to name a few.

Figure 6A:
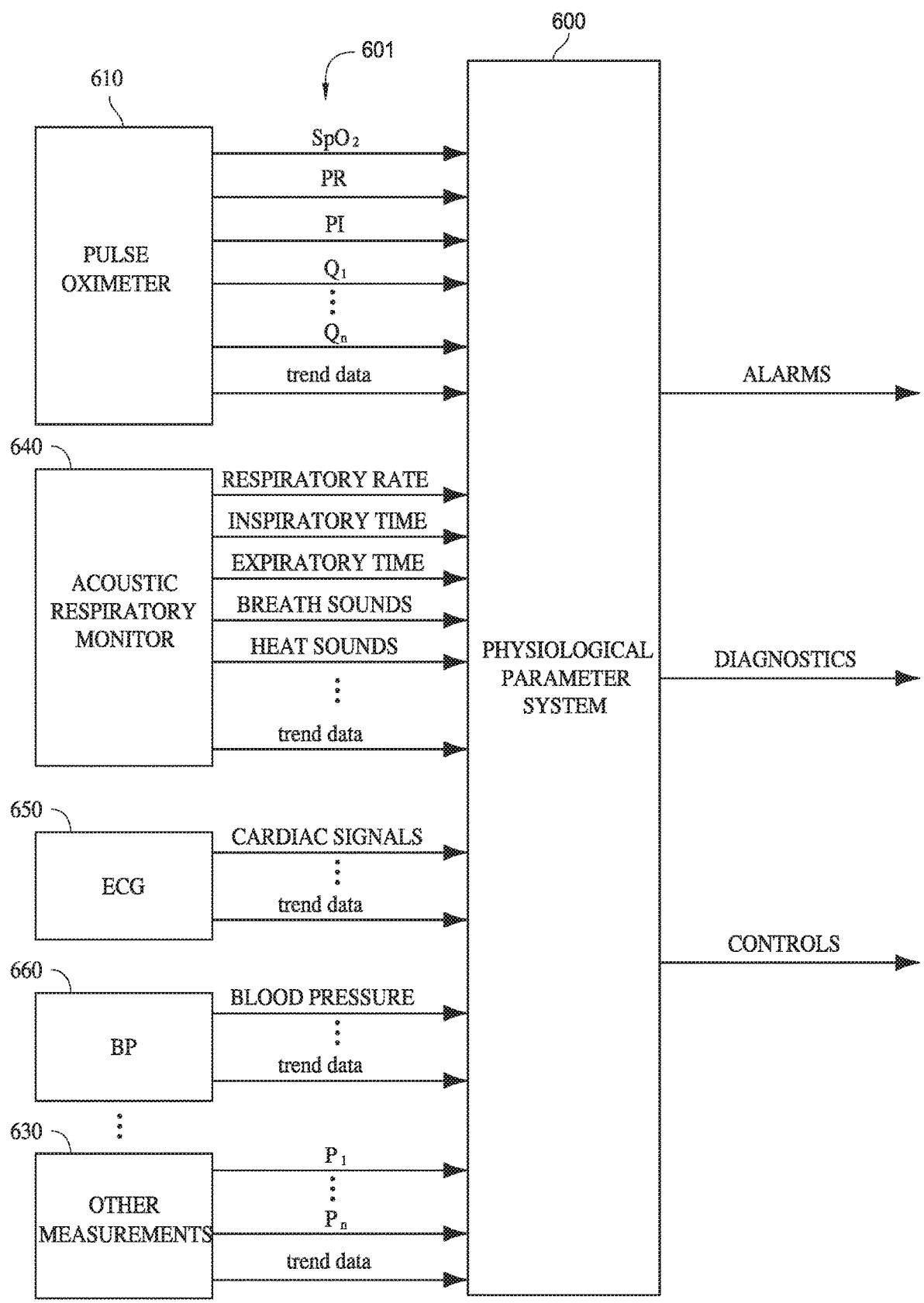
FIG. 6A illustrates an embodiment of a physiological parameter system 600 similar to the system in FIG. 6

FIG. 6A illustrates an embodiment of a physiological parameter system 600 similar to the system in FIG. 6. The physiological parameter system 600 has as inputs 601 from one or more parameters from one or more physiological measurement devices, such as, for example a pulse oximeter 610, an acoustic respiratory monitor 640, an ECG monitor 650, an invasive or non-invasive blood pressure monitor 650, a thermometer, or any other invasive or noninvase physiological monitoring devices or the like.

Figure 7:
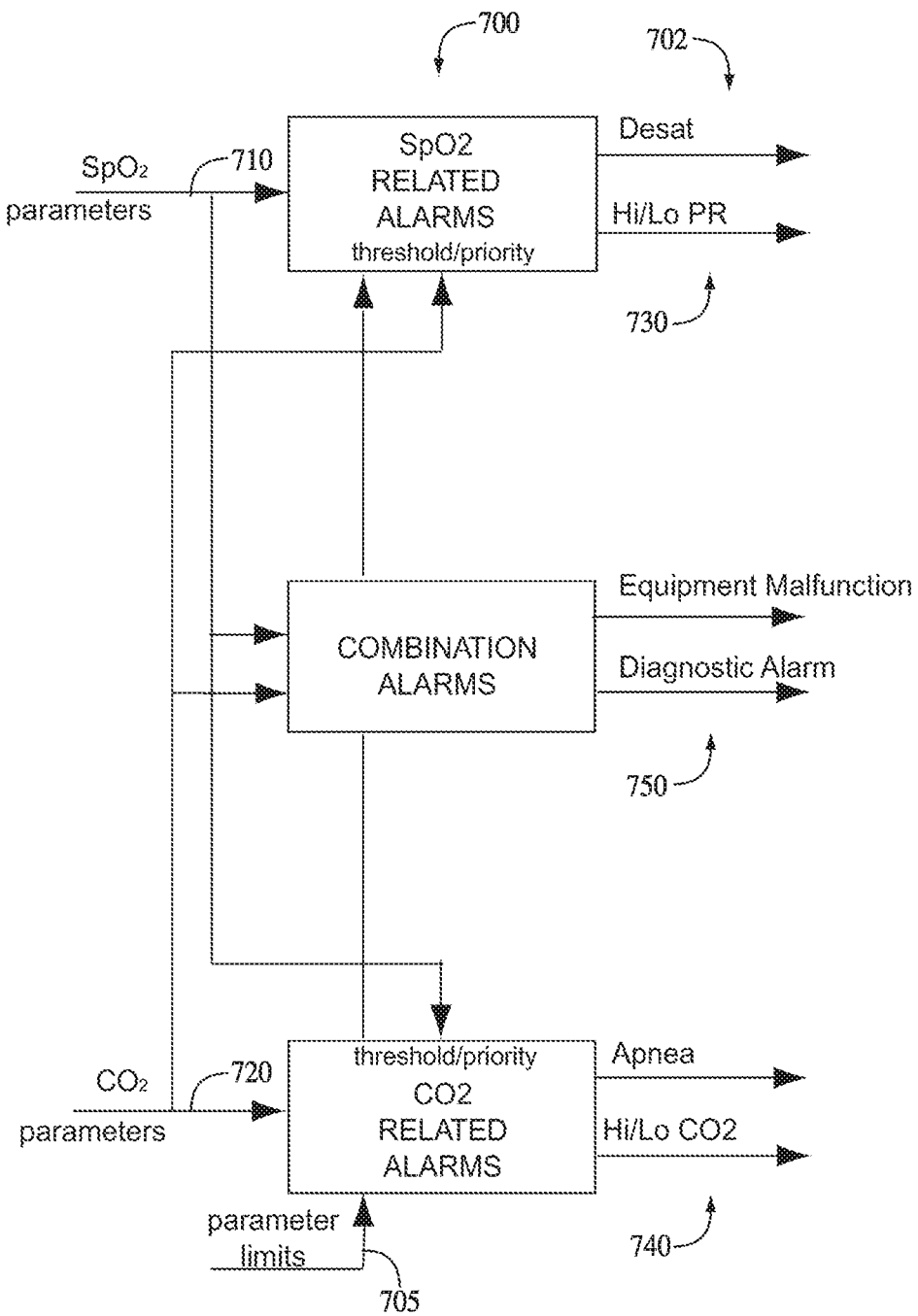
FIG. 7 is a block diagram of a physiological parameter system combining pulse oximetry and capnography and providing alarm outputs.

FIG. 7 illustrates one embodiment of a physiological parameter system 700 combining pulse oximetry parameter inputs 710 and capnography parameter inputs 720 so as to generate alarm outputs 702. Parameter limits 705 may be user inputs, default conditions or otherwise predetermined alarm thresholds for these parameters 710, 720. The alarms 702 are grouped as pulse oximetry related 730, capnography related 740 and a combination 750. For example, a pulse oximetry alarm 730 may be related to percent oxygen saturation and trigger when oxygen saturation falls below a predetermined percentage limit. A capnography alarm 740 may be related to $ETCO_2$ and trigger when $ETCO_2$ falls below or rises above a predetermined mm Hg pressure limit. A combination alarm 750 may indicate a particular medical condition related to both pulse oximetry and capnography or may indicate a malfunction in either instrument.

Figure 8:
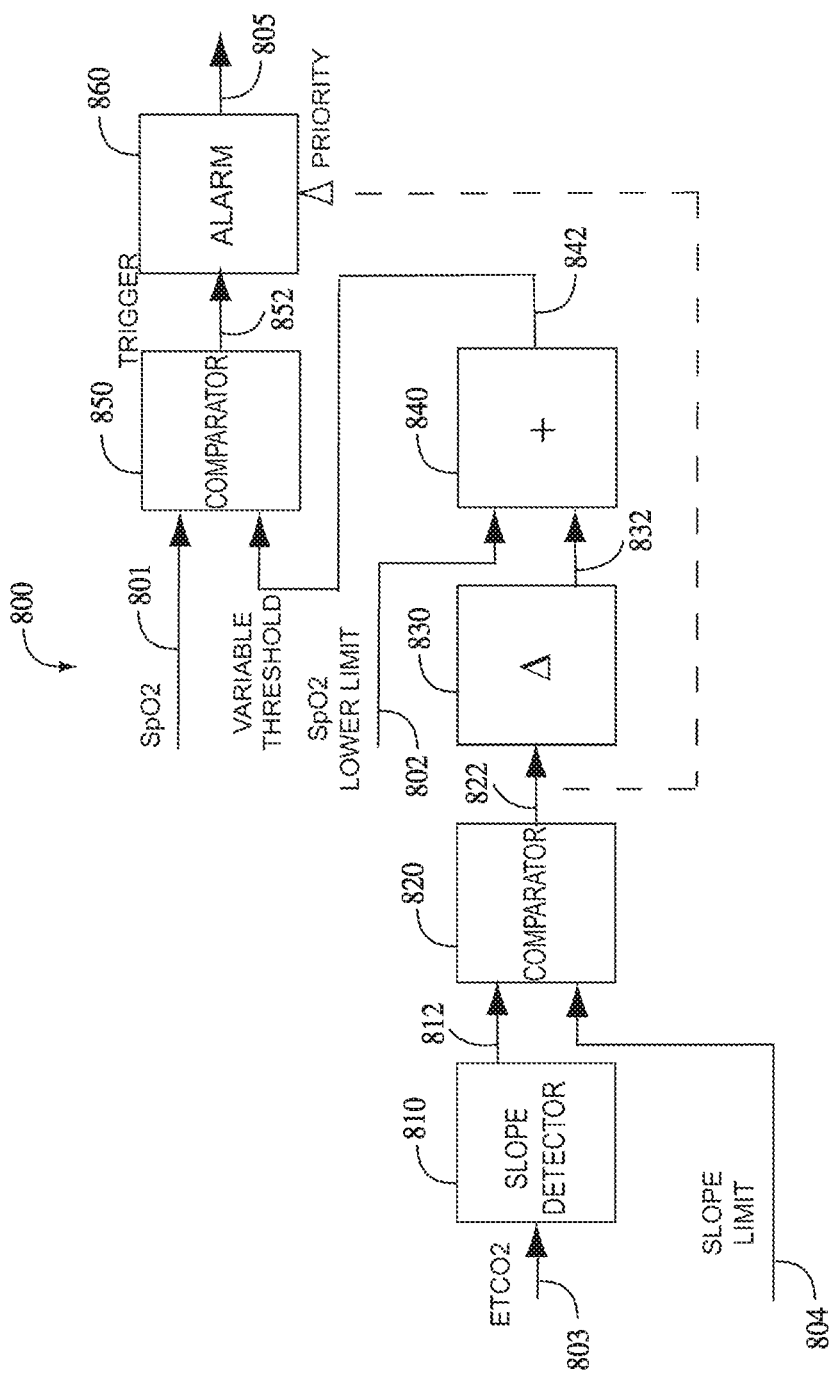
FIG. 8 is a block diagram of a saturation limit alarm enhanced by $ETCO_2$ measurements.

FIG. 8 illustrates a $SpO_2$ alarm embodiment 800 that is responsive to $ETCO_2$. In particular, a $SpO_2$ alarm 805 may be triggered sooner and may indicate a high priority if $ETCO_2$ 803 is falling. That is, if $ETCO_2$ 803 is trending down above a certain rate, the $SpO_2$ alarm 805 is triggered at a higher percentage oxygen saturation threshold and alerts a caregiver to the possibility of a serious condition, e.g. a pulmonary embolism.

As shown in FIG. 8, a slope detector 810 determines the slope 812 of the $ETCO_2$ input 803. A slope comparator 820 compares this slope 812 to a predetermined slope limit 804. If the downward trend of $ETCO_2$ 803 is great enough, a delta value 803 is added 840 to the $SpO_2$ lower limit 802 to generate a variable threshold 842. A threshold comparator 850 compares this variable threshold 842 to the $SpO_2$ input 801 to generate a trigger 852 for the $SpO_2$ alarm 805. The alarm volume, modulation or tone may be altered to indicate priority, based upon the slope comparator output 822.

Figure 9:
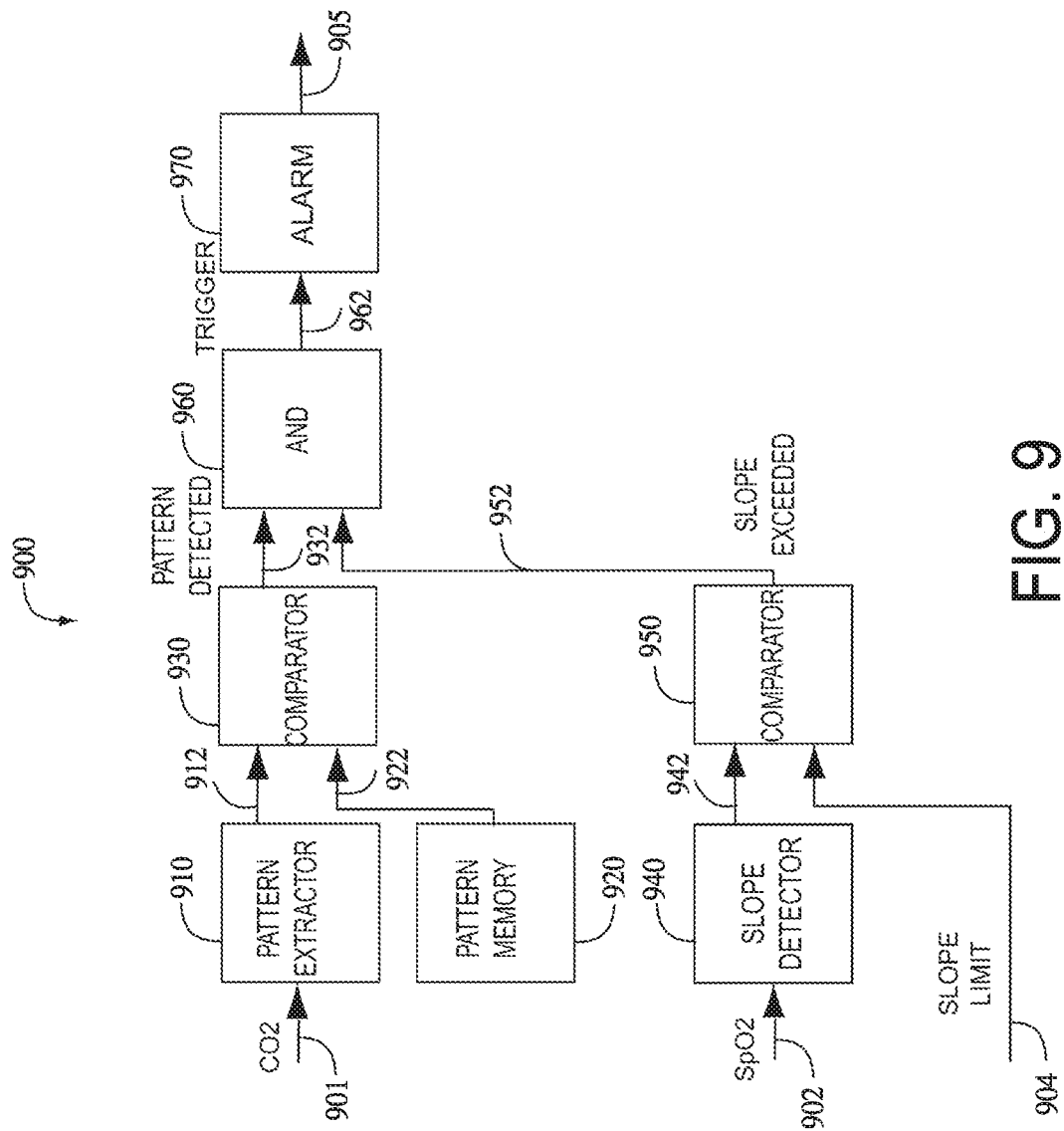
FIG. 9 is a block diagram of a $CO_2$ waveform alarm enhanced by $SpO_2$ measurements.

FIG. 9 illustrates a $CO_2$ alarm embodiment 900 that is responsive to $SpO_2$. In particular, morphology of the input $CO_2$ waveform 901 is utilized to trigger an alarm 905, and that alarm is also responsive to a falling $SpO_2$ 902. That is, if a pattern in the $CO_2$ waveform is detected and $SpO_2$ is trending down above a certain rate, then an alarm is triggered. For example, an increasing slope of the $CO_2$ plateau in combination with a downward trend of $SpO_2$ may trigger an alarm and alert a caregiver to the possibility of an airway obstruction.

As shown in FIG. 9, a pattern extractor 910 identifies salient features in the $CO_2$ waveform and generates a corresponding feature output 912. A pattern memory 920 stores one or more sets of predetermined waveform features to detect in the $CO_2$ input 901. The pattern memory 920 is accessed to provide a feature template 922. A feature comparator 930 compares the feature output 912 with the feature template 922 and generates a match output 932 indicating that a specific shape or pattern has been detected in the $CO_2$ waveform 901. In addition, a slope detector 940 determines the slope 942 of the $SpO_2$ input 902. A slope comparator 950 compares this slope 942 to a predetermined slope limit 904. If the downward trend of $SpO_2$ 902 is great enough, a slope exceeded output 952 is generated. If both the match output 932 and the slope exceeded output 952 are each asserted or "true," then a logical AND 960 generates a trigger output 96 to the alarm 970, which generates an alarm output 905.

Figure 10:
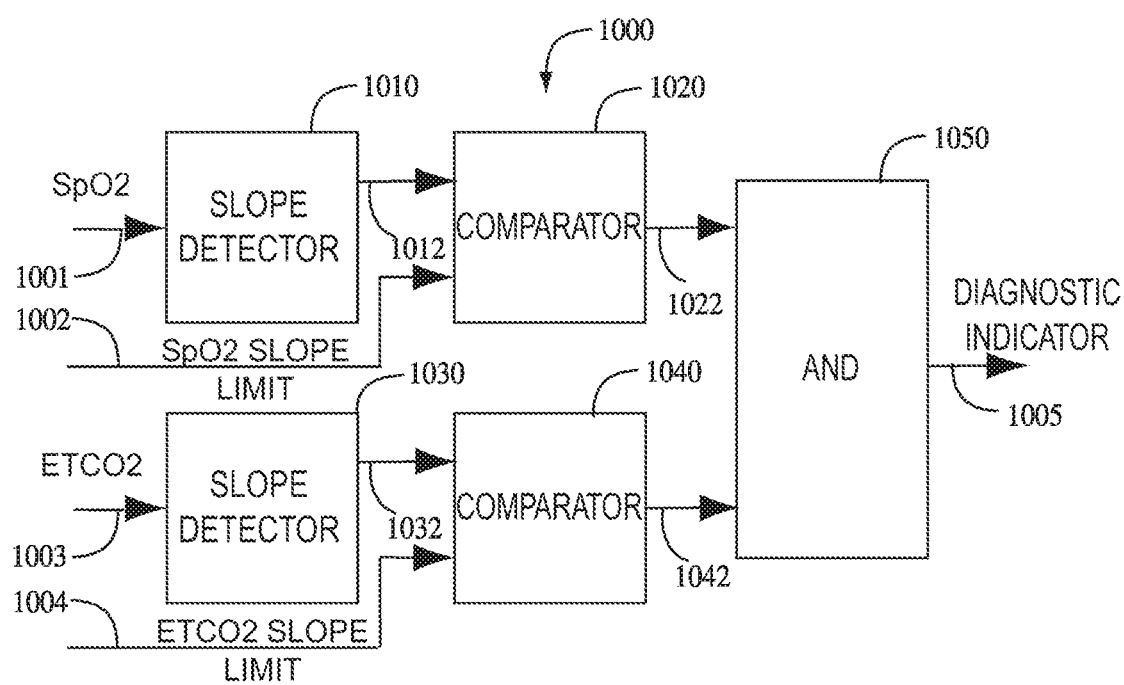
FIG. 10 is a block diagram of a physiological parameter system combining pulse oximetry and capnography and providing a diagnostic output.

FIG. 10 illustrates a combination embodiment 1000 having a diagnostic output 1005 responsive to both $SpO_2$ 1001 and $CO_2$ 1003 inputs. A $SpO_2$ slope detector 100 determines the slope 102 of the $SpO_2$ input 1001 and can be made responsive to a negative slope, a positive slope or a slope absolute value. A first comparator 1020 compares this slope 102 to a predetermined $SpO_2$ slope limit 1002. If the trend of $SpO_2$ 1001 is great enough, a $SpO_2$ slope exceeded output 1022 is asserted. Likewise, an $CO_2$ slope detector 1030 determines the slope 1032 of the $CO_2$ input 1003. A second comparator 1040 compares this slope 1032 to a predetermined $CO_2$ slope limit 1004. If the downward trend of $CO_2$ 1001 is great enough, an $CO_2$ slope exceeded output 1042 is asserted. If both slope exceeded outputs 1022, 1042 are asserted or "true," a diagnostic output 1005 is asserted.

In one embodiment, the slope detectors 610, 1030 are responsive to a negative trend in the $SpO_2$ 1001 and $CO_2$ 1003 inputs, respectively. Accordingly, the diagnostic output 1005 indicates a potential embolism or cardiac arrest. In another embodiment, the $SpO_2$ slope detector 610 is responsive to negative trends in the $SpO_2$ 1001 input, and the $CO_2$ slope detector 1030 is responsive to a positive trend in the $CO_2$ 1003 input. Accordingly, the diagnostic output 1005 indicates a potential airway obstruction. The diagnostic output 1005 can trigger an alarm, initiate a display, or signal a nursing station, to name a few.

Figure 11A:
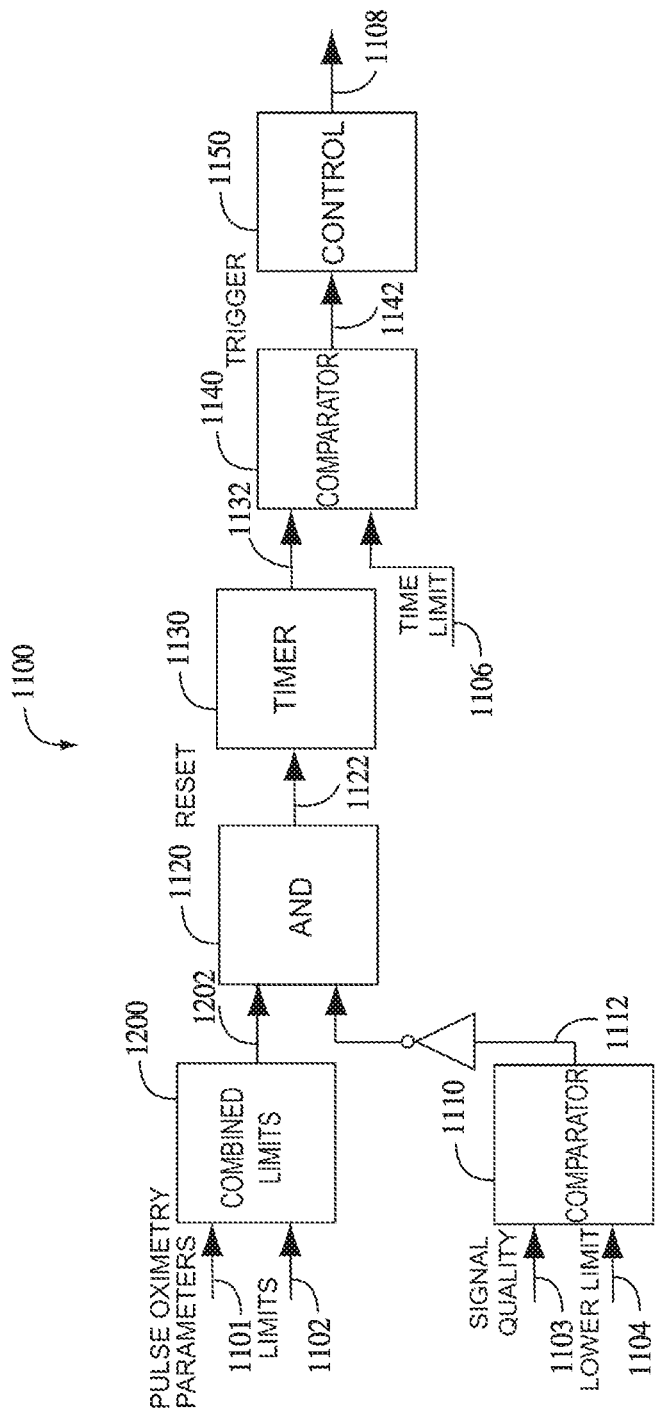
FIGS. 11A, 11B, 12 are block diagrams of a physiological parameter system utilizing pulse oximetry to control patient controlled analgesia (PCA).
Figure 11B:
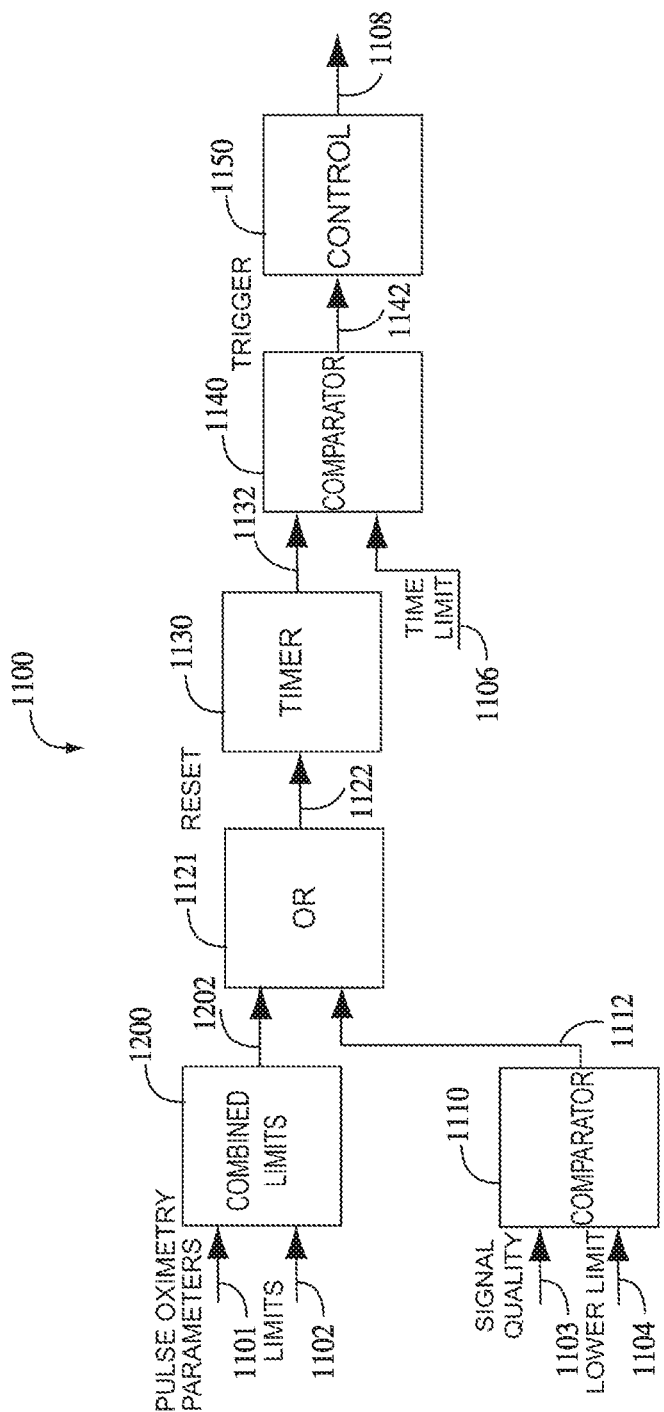

FIGS. 11A-B illustrate a physiological parameter system 1100 utilizing pulse oximetry to control patient controlled analgesia (PCA). In particular embodiments, a control output 1108 is responsive to pulse oximetry parameters 1101 only if signal quality 1103 is above a predetermined threshold 1104. In FIG. 11A, the control output 1108 can be used to lock-out patient controlled analgesia (PCA) if pulse oximetry parameter limits have been exceeded. If signal quality is so low that those parameters are unreliable, however, PCA is advantageously allowed. That is, the pulse oximeter parameters are not allowed to lock-out PCA if those parameters are unreliable. By contrast, in FIG. 11B, the control output 1108 can be used to advantageously lock-out or disable patient controlled analgesia (PCA) if pulse oximetry parameter limits have been exceeded or if signal quality is so low that those parameters are unreliable.

As shown in FIG. 11A, pulse oximetry parameters 1101 and corresponding limits 1102 for those parameters are one set of inputs and a signal quality measure 1103 and a corresponding lower limit 1104 for signal quality are another set of inputs. The parameters 1101 and corresponding limits 1102 generate a combined output 1202 that is asserted if any of the pulse oximetry parameter limits are exceeded. A comparator 1110 compares the signal quality 1103 input with a lower limit 1104 generating a quality output 1112 that is asserted if the signal quality 1103 drops below that limit 1104. An AND logic 1120 generates a reset 1122 if the combined output 1202 is asserted and the quality output 1112 is not asserted. The reset 1122 resets the timer 1130 to zero. A comparator 1140 compares the timer output 1132 to a predetermined time limit 1106 and generates a trigger 1142 if the time limit is exceeded. The trigger 1142 causes the control 1150 to generate the control output 1108, enabling a patient controlled analgesia (PCA), for example. In this manner, the PCA is enabled if all monitored parameters are within set limits and signal quality is above its lower limit for a predetermined period of time.

As shown in FIG. 11B, the combined output 1202, quality output 1112, reset 1122, timer 1130, comparator 1140 and control 1150 are generated as described with respect to FIG. 11A, above. An OR logic 1121 generates a reset 1122 if either the combined output 1202 or the quality output 1112 is asserted. In this manner, the PCA is disabled for a predetermined period of time if any of the monitored parameters are outside of set limits or the signal quality is below its lower limit.

Figure 12:
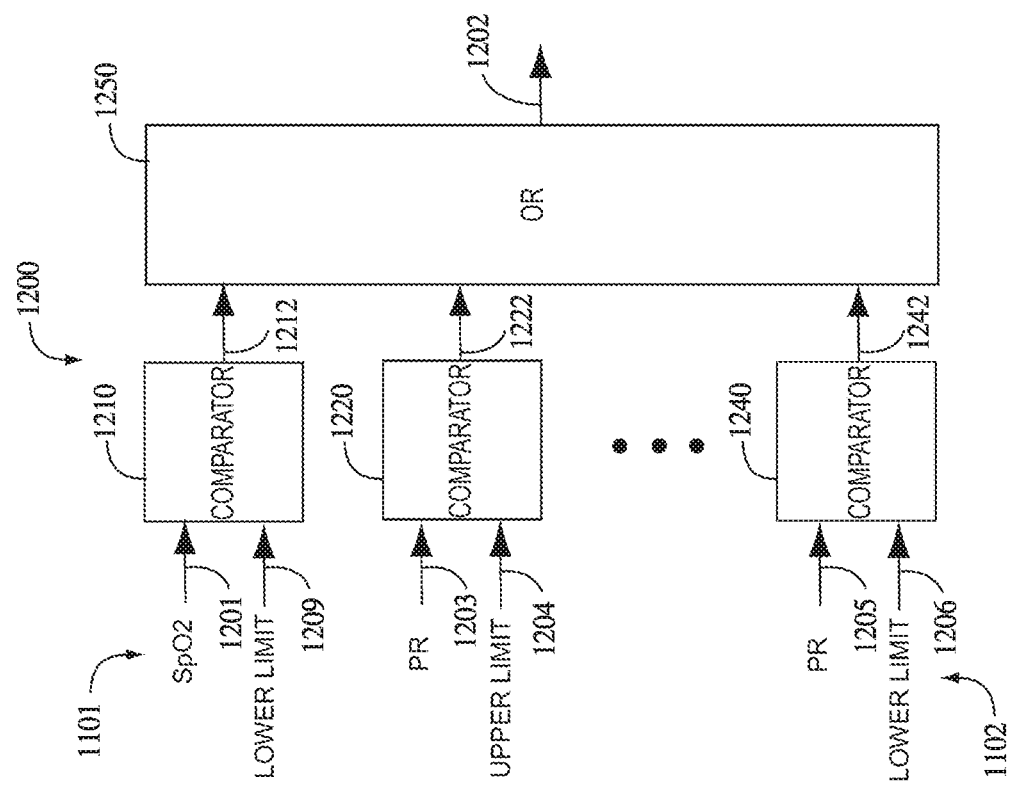

FIG. 12 illustrates combined limits 1200 having $SpO_2$ parameters 1101 and corresponding thresholds 1102 as inputs and providing a combination output 1202. In particular, if any parameter 1101 exceeds its corresponding limit 1102, the output of the corresponding comparator 1210, 1220, 1240 is asserted. An OR logic 1250 is responsive to any asserted output 1212, 1222, 1242 to asserted the combined output 1202. For example, the combined output 1202 may be asserted if $SpO_2$1201 falls below a lower limit 1209, pulse rate (PR) 1203 rises above an upper limit 1204 or PR 1203 falls below a lower limit 120.

A physiological parameter system has been disclosed in detail in connection with various embodiments. These embodiments are disclosed by way of examples only and are not to limit the scope of the claims that follow. One of ordinary skill in the art will appreciate many variations and modifications. For example, the control output 1108 (FIG. 11B) can be used to control (titrate) delivered, inspired oxygen levels to patients based upon pulse oximetry parameters, unless signal quality is so low that those parameters are unreliable. One of ordinary skill in the art will also recognize that the control output 1108 (FIG. 11B) can be used to control patient delivery of any of various pharmacological agents and/or medical gases.

Figure 13:
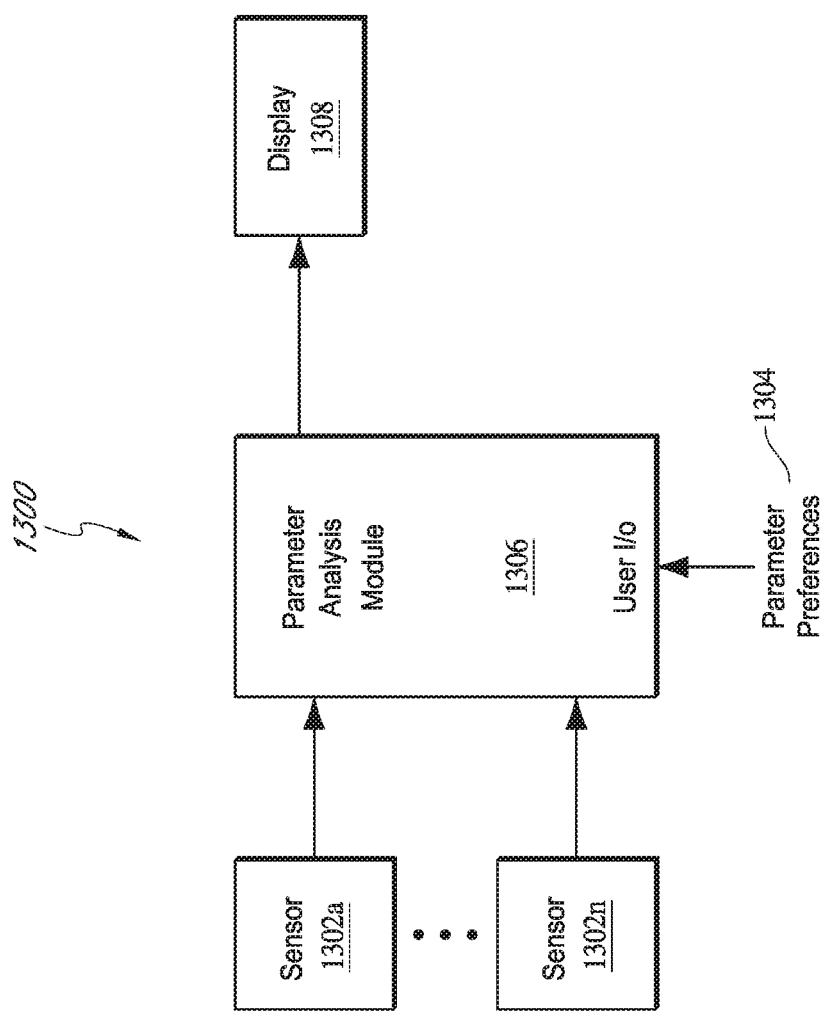
FIGS. 13, 13A, 13B illustrates an embodiment of a system that displays an indicator of the wellness of a patient.

FIG. 13 illustrates an embodiment of a system 1300 that displays an indicator of the wellness of a patient. Various sensors 1302a-1302n communicate with a parameter analysis module 1306. Sensors 1302a-1302n may include pulse oximeters and capnometers, among other physiological parameter measurement devices. Sensor 1302n outputs a signal that may be sampled, normalized, and/or analyzed by modules that are not shown in system 1300 before being passed to parameter analysis module 1306. As described above, normalization of sensor signals before comparison of the signals to parameter limits 452 (FIG. 4) and/or parameter preferences 1304 may have certain benefits, such as decreased incidence of false alarms and/or more effective determination of the wellness of the patient.

In the embodiment shown, a user may provide parameter preferences 1304 to parameter analysis module 1306 through a user interface. Parameter preferences 1304 may include preferred ranges, less preferred ranges, least preferred ranges, upper limits, lower limits, preferred rates of increase or decrease, preferred patterns or trends, preferred states, or any combination of such preferences or other standards for evaluating the desirability of various physiological parameter values and signals. In some cases, a user of system 1300 may provide custom preferences to override a default set of physiological parameter preferences 1304 preprogrammed into system 1300. In some embodiments, parameter analysis module 1306 may include program code for dynamically changing or suggesting changes to various parameter preferences as a function of certain physiological parameters or related sensor performance data.

Figure 13A:
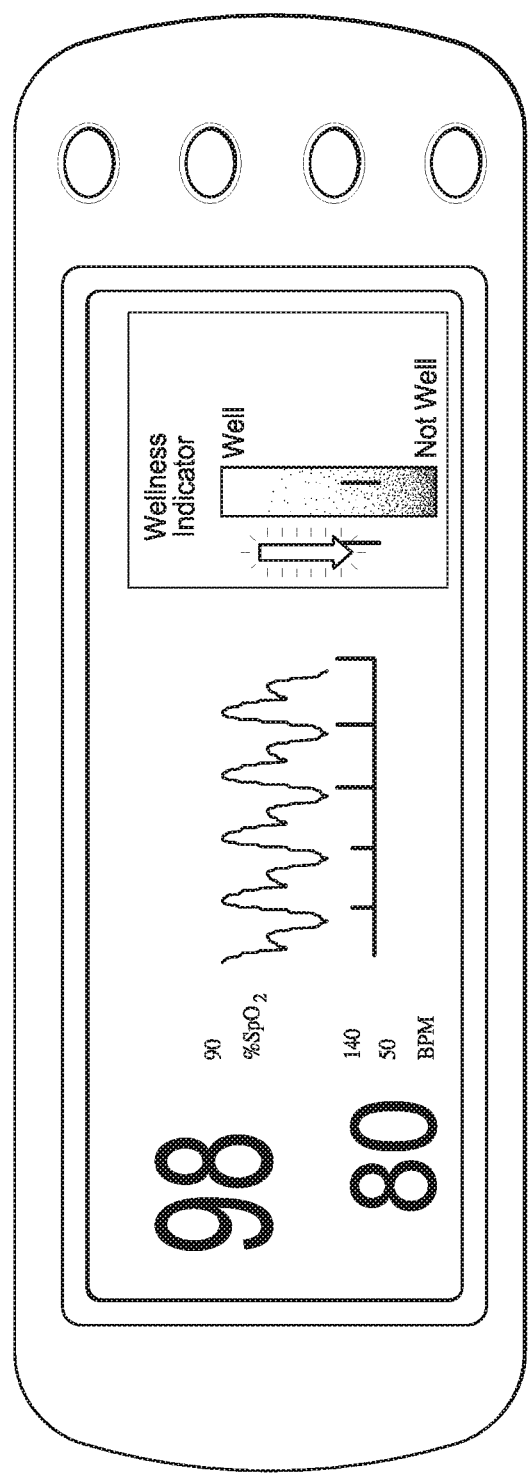
Figure 13B:
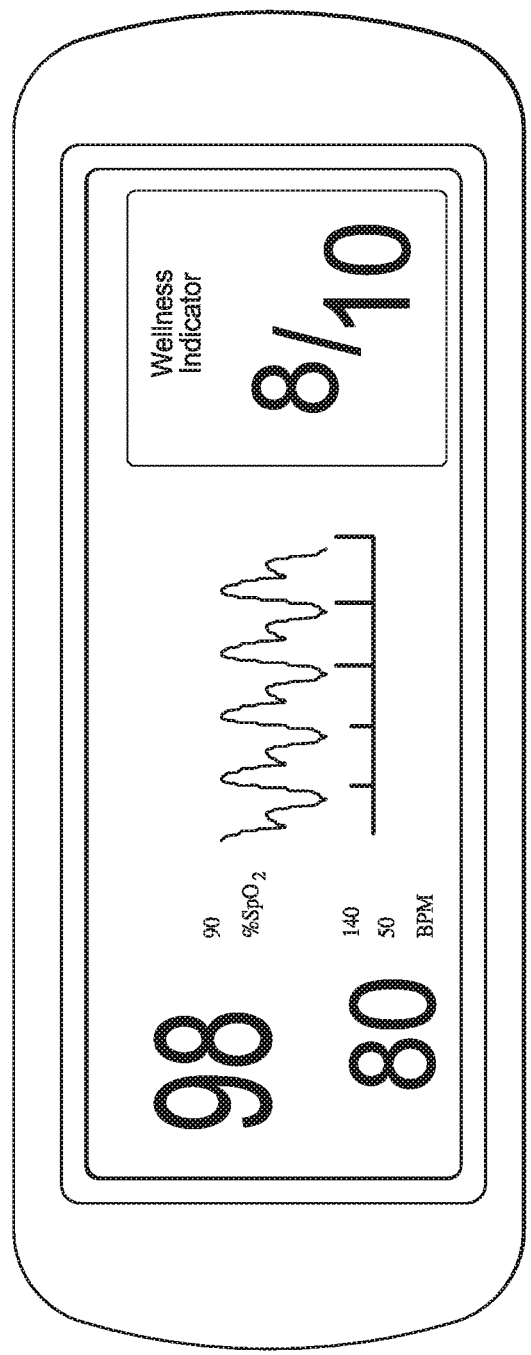

Parameter analysis module 1306 compares at least some of the signal data received from sensors 1302a-1302n to parameter preferences 1304 in order to calculate an indicator of the wellness of a patient. In some embodiments, the indicator calculated is a numerical indicator; for example, a number between one and ten, where a ten corresponds to a patient with a high level of wellness, and a one corresponds to a patient with a very low level of wellness as depicted in FIG. 13B. Other ranges, such as one to 100, −100 to 100, etc., and scales, such as an alphabetic A-F scale or a color scale, may also be used including the scale depicted in FIG. 13A. Other indicators that may be generated by parameter analysis module 1306 include graphical indicators of potential trouble areas, gauges, charts, level meters, and the like may also be used. Parameter analysis module 1306 communicates the indicator to a display 1308, which may display the indicator in any suitable graphical or textual form that is known in the art. For example, display 1308 may show a number of bars or a level meter, the number of which may correspond to one of the numerical indicator scales discussed above.

Figure 14:
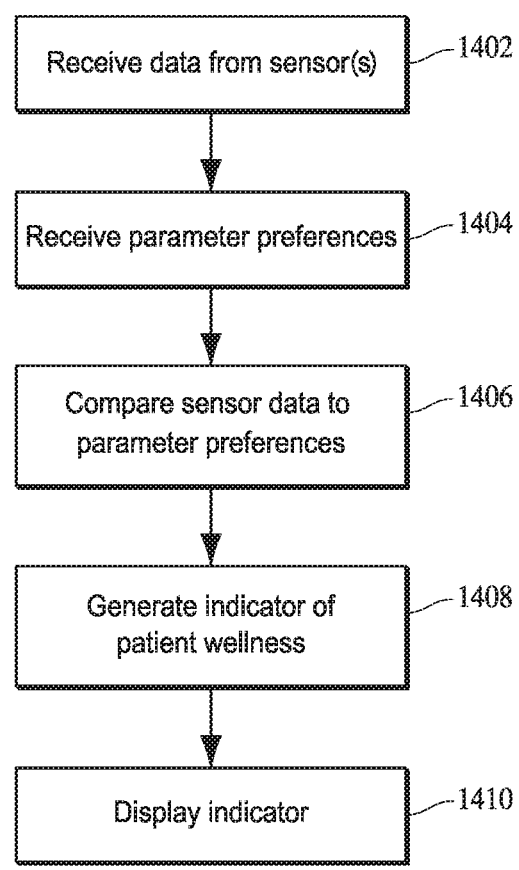
FIG. 14 is a flowchart showing an example method of displaying an indicator of the wellness of a patient.

FIG. 14 is a flowchart showing an example method of displaying an indicator of the wellness of a patient. At step 1402, parameter analysis module 1306 (FIG. 13) receives signal data from one or more sensors 1302a-1302n. As discussed previously, such signal data may be normalized or otherwise modified from its raw form before being passed to parameter analysis module 1306. Parameter analysis module 1306 may continuously update an indicator as new data is received and may calculate averages, variances, and/or other analytical measures of various physiological parameters over time. In some embodiments, parameter analysis module 1306 may update the indicator of patient wellness only periodically, sporadically, or by request rather than continuously, thus requiring only occasional reception of data from sensors 1302a-1302n.

In step 1404, parameter analysis module 1306 receives parameter preferences 1304. Preferences 1304 may by received only once or sporadically as a user supplies custom preferences. Preferences 1304 may also be received and/or updated continuously when, for example, parameter preferences 1304 are functions of various physiological or sampling parameters.

At step 1406, parameter analysis module 1306 compares the data received from sensors 1302a-1302n to parameter preferences 1304. Individual sensor measurements may be compared to parameter preferences 1304, or parameter analysis module may compare parameter preferences 1304 to a moving average of sensor measurements, for example. Comparison of various other known analytical measures of sensor data is also possible and within the scope of the present disclosure. The comparison performed by parameter analysis module 1306 may include magnitude comparisons, pattern analysis, and/or trend analysis. Historical sensor data may also be used in the comparison.

In step 1408 of FIG. 14, parameter analysis module 1306 generates an indicator of the wellness of the patient based on the comparison performed in step 1406. The indicator may be in any of the forms discussed previously. For example, module 1306 may increase a wellness score (e.g., a numerical indicator of wellness) when physiological parameters fall within preferred ranges or when sensor signals follow preferred patterns and/or trends. The indicator may comprise a simple or a more detailed textual and/or graphical summary of the patient's wellness as interpreted from parameters measured by sensors 1302a-1302n. In some embodiments, the indicator may be a scaled number in combination with a textual description of the patient's wellness score and/or conditions that may be affecting the score. In addition, particular a particular condition affecting the patient can also be generated for communication to a healthcare provider, such as, for example, sepsis, septic shock, apnea, heart failure, airway obstruction, carbon monoxide poisoning, low oxygen content, etc.

After parameter analysis module 1306 generates the wellness indicator, it sends the indicator to display 1308 at step 1410. Display 1308 may be integrated with physiological parameter system 1300 or may be a separate display device. The display may also include auditory sounds, such as for example, beeps, voices, words, etc., to indicate a particular event or condition occurring.

Although the foregoing invention has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. It is contemplated that various aspects and features of the invention described can be practiced separately, combined together, or substituted for one another, and that a variety of combination and subcombinations of the features and aspects can be made and still fall within the scope of the invention. Furthermore, the systems described above need not include all of the modules and functions described in the preferred embodiments. Accordingly, the present invention is not intended to be limited by the recitation of the preferred embodiments, but is to be defined by reference to the appended claims.

What is claimed is:

1. A system for indicating a wellness state of a patient comprising:
 a first sensor configured to measure a first physiological parameter and output an indication of the first physiological parameter;
 a second sensor configured to measure a second physiological parameter different from said first physiological parameter and output an indication of the second physiological parameter; and
 a processor which receives the outputs of the first and second sensor, determines an indication of wellness from the outputs, and outputs the indication of wellness to a display device, said processor further configured to change a first alarm threshold corresponding to the first physiological parameter based on a first trend in the second physiological parameter.

2. The system of claim 1, wherein the first sensor comprises a pulse oximeter and the second sensor comprises a capnograph.

3. The system of claim 1, wherein the pulse oximeter sensor is configured to output oxygen saturation.

4. The system of claim 3, wherein the capnograph is configured to output an exhaled gas parameter.

5. The system of claim 4, wherein the exhaled gas parameter comprises exhaled $CO_2$.

6. The system of claim 5, wherein the first trend comprises a downward trend in exhaled CO2 and the first physiological parameter comprises oxygen saturation.

7. The system of claim 1, wherein the indication of wellness comprises a numerical indicator, alphabetic indicator, or a color indicator.

8. The system of claim 1, wherein the indication of wellness comprises a textual description of the patient's wellness state.

9. The system of claim 1, wherein the process further determines conditions of the patient from the outputs.

10. The system of claim 9, wherein the conditions of the patient comprise sepsis, septic shock, apnea, heart failure, airway obstruction, carbon monoxide poisoning, or low oxygen content.

\* \* \* \* \*